United States Patent
Caenepeel et al.

(10) Patent No.: US 10,328,062 B2
(45) Date of Patent: *Jun. 25, 2019

(54) BIOMARKERS AND USE OF MET INHIBITOR FOR TREATMENT OF CANCER

(71) Applicant: AMGEN, INC., Thousand Oaks, CA (US)

(72) Inventors: Sean Caenepeel, Woodland Hills, CA (US); Angela Coxon, Moorpark, CA (US); Zhiqiang Du, Thousand Oaks, CA (US); Paul Hughes, Santa Monica, CA (US); Robert Loberg, Thousand Oaks, CA (US); Gataree Ngarmchamnanrith, Thousand Oaks, CA (US); Beate Sable, Newbury Park, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/300,690

(22) PCT Filed: Apr. 3, 2015

(86) PCT No.: PCT/US2015/024306
§ 371 (c)(1),
(2) Date: Sep. 29, 2016

(87) PCT Pub. No.: WO2015/154005
PCT Pub. Date: Oct. 8, 2015

(65) Prior Publication Data
US 2017/0182016 A1 Jun. 29, 2017

Related U.S. Application Data

(60) Provisional application No. 61/975,487, filed on Apr. 4, 2014, provisional application No. 61/993,871, filed on May 15, 2014.

(51) Int. Cl.
*A61K 31/4375* (2006.01)
*C12Q 1/6886* (2018.01)

(52) U.S. Cl.
CPC ........ *A61K 31/4375* (2013.01); *C12Q 1/6886* (2013.01); *C12Q 2600/106* (2013.01); *C12Q 2600/154* (2013.01); *C12Q 2600/158* (2013.01)

(58) Field of Classification Search
CPC .................................................. A61K 31/4375
USPC .......................................................... 514/300
See application file for complete search history.

(56) References Cited

U.S. PATENT DOCUMENTS

| | | | |
|---|---|---|---|
| 7,932,026 B2* | 4/2011 | Seshagiri | C12Q 1/485 435/287.1 |
| 8,198,448 B2* | 6/2012 | Albrecht | C07D 471/04 546/119 |
| 2006/0246492 A1* | 11/2006 | Haber | C12Q 1/6886 435/6.14 |
| 2013/0225424 A1* | 8/2013 | Bacus | C12Q 1/6886 506/7 |

FOREIGN PATENT DOCUMENTS

| WO | 2013/007808 A1 | 1/2013 |
| WO | 2013/120018 A1 | 8/2013 |
| WO | 2016044772 A2 | 3/2016 |

OTHER PUBLICATIONS

Janjigian et al. 99th AACR Annual Meeting Apr. 12-16, 2008.*
PCT Notification of Transmittal of the International Search Report and Written Opinion, PCT International Search Report and PCT Written Opinion issued for the corresponding PCT application No. PCT/US15/24306, dated Jul. 13, 2015 (8 pages).
Wang et al., "SU5416 is a potent inhibitor of hepatocyte growth factor receptor (c-Met) and blocks HGF-induced invasiveness of human HepG2 hepatoma cells," Journal of Hepatology, 2004, vol. 41, No. 2, pp. 267-273.
Xu et al, "Expression of the c-Met oncogene by tumor cells predicts a favorable outcome in classical Hodgkin's lymphoma," Haematologica, Apr. 2012, vol. 97, No. 4, pp. 572-578.
Jochen K. Lennerz, et al., "MET Amplification Identifies a Small and Aggressive Subgroup of Esophagogastric Adenocarcinorna With Evidence of Responsiveness to Crizotinib," Journal of Clinical Oncology, vol. 29, No. 36, Dec. 20, 2011 (pp. 4803-4810).
P.E. Hughes et al., "In Vitro and In Vivo Activity of AMG 337, a Potent and Selective MET Kinase Inhibitor, in MET-Dependent Cancer Models", Molecular Cancer Therapeutics, vol. 15, No. 7, Apr. 19, 2016 (pp. 1568-1579).
The Extended European Search Report dated Jan. 18, 2018 for the corresponding Application No. PCT/US2015024306 (12 pages).

\* cited by examiner

*Primary Examiner* — Nizal S Chandrakumar
(74) *Attorney, Agent, or Firm* — Lucas & Mercanti, LLP

(57) ABSTRACT

The present invention relates to methods of therapeutic treatment of cancer using selective tyrosine kinase inhibitors and cancer biomarkers, such as MET amplification and high Met expression for patient selection.

9 Claims, 18 Drawing Sheets

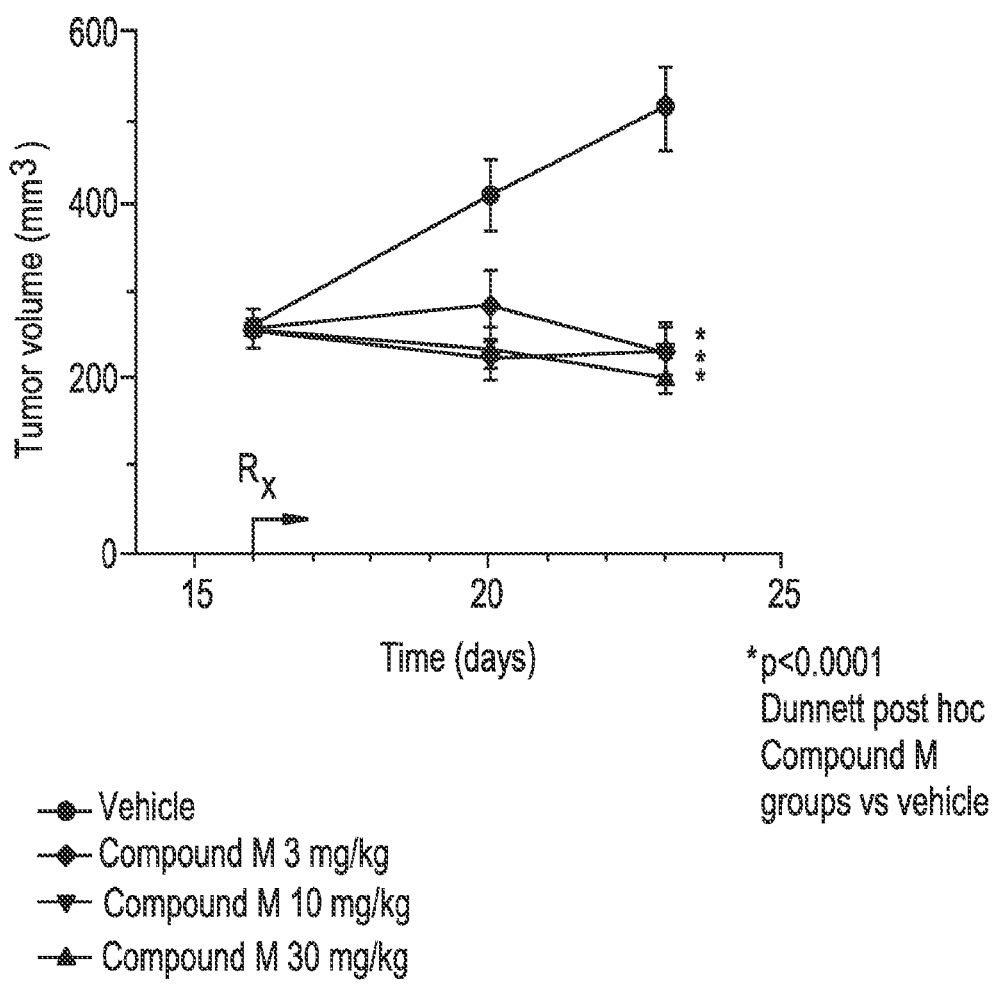

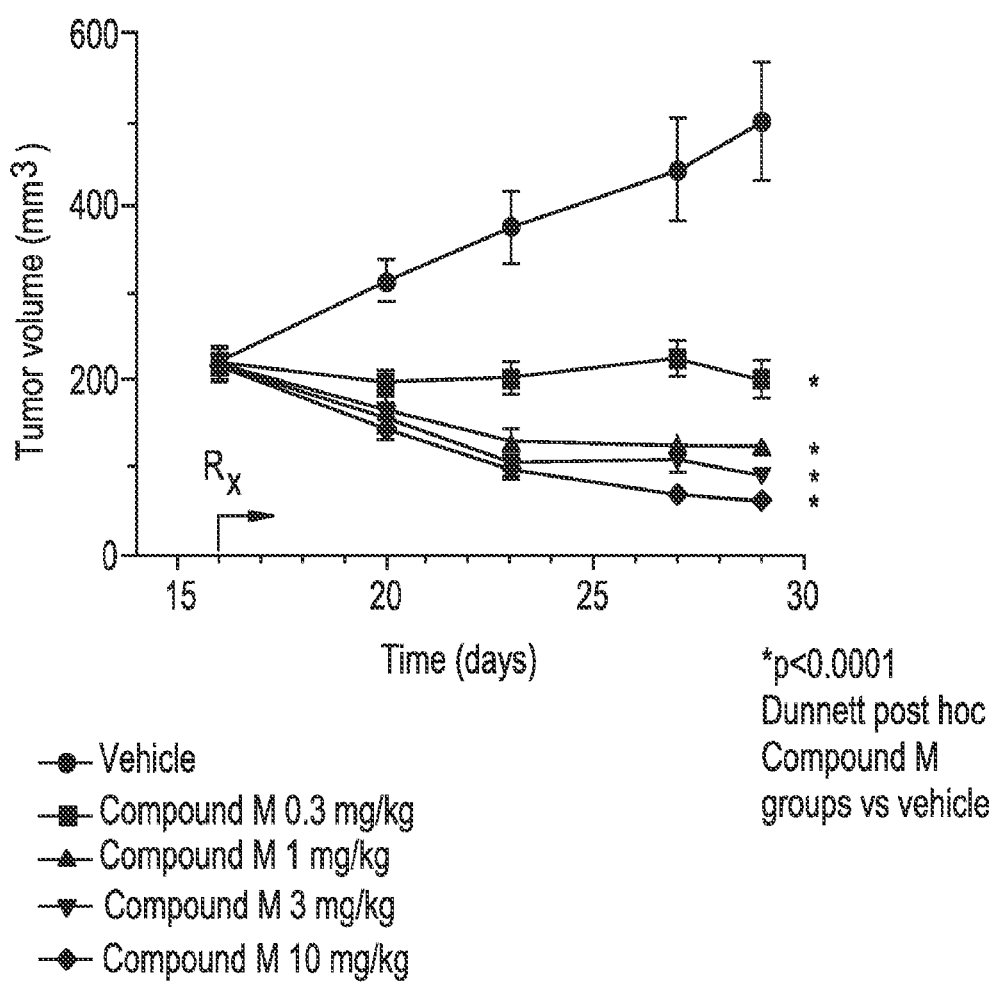

BIOMARKERS AND USE OF MET INHIBITOR FOR TREATMENT OF CANCER

CROSS-REFERENCE TO RELATED APPLICATIONS

This application is a 371 of PCT/US2015/024306, filed Apr. 3, 2015, which claims the benefit of U.S. Provisional Patent Application Ser. Nos. 61/975,487, filed Apr. 4, 2014 and 61/993,871, filed May 15, 2014.

FIELD

The present invention relates to methods of therapeutic treatment of cancer and cancer biomarkers, such as MET amplification and Met expression as biomarkers for patient selection. The present invention also relates to articles of manufacture.

BACKGROUND

Cancer is the leading cause of death after heart disease in the U.S. Although progress has been made in the diagnosis and treatment of various cancers, these diseases still result in significant morbidity. Esophageal and gastric cancers are among the most highly lethal types of cancer worldwide, with an annual incidence of approximately 1.5 million cases. The five-year relative survival rate for gastric cancer cases diagnosed in the United States has improved only from 16% to 24% over the last 30 years (Jemal, A. et al. Cancer statistics, 2007. *CA Cancer J Clin.* 2007:57, 43-46), highlighting the need for more effective therapies. In addition, in Western countries, there has been a steady rise in adenocarcinomas of the gastric cardia and gastroesophageal junction, which has been associated with increased body mass index (Merry, A., et al. Gut. 2007:56, 1503-1511). Gene amplification is one of the most frequent genetic alterations in gastric cancer and is believed to play a major role in its development and progression.

Lung cancer is a heterogeneous group of disorders that is subdivided into molecular subtypes with dedicated targeted therapies. Non-small cell lung cancer (NSCLC) is a common cancer with high mortality and few effective treatment options. NSCLC includes diverse types of diseases such as adenocarcinoma, squamous cell carcinoma, undifferentiated large cell carcinoma, adenosquamous carcinoma (pleiomorphic carcinoma), sarcomatoid carcinoma and others.

MET encodes a transmembrane tyrosine kinase receptor for Hepatocyte Growth Factor (HGFR), which is implicated in various oncogenic processes including cell proliferation, survival, invasion, motility and metastasis. MET can be activated either by binding to its ligand HGF, high Met expression/amplification, mutation, or decreased degradation. These mechanisms for MET activation are now being therapeutically targeted in vitro, in tumor xenograft models, in vivo and in clinical trials. High expression and amplification are different phenomena and present different diagnostic targets and/or treatment opportunities. High expression or over expression can result from a single unamplified gene, and an amplified gene does not always lead to greater expression levels of mRNA and protein. Thus, it is not possible to predict whether one phenomenon will lead to another, or whether they are related. However, amplification and high expression can be indicative of certain cancers and precancers. In particular, recent findings underscore the prognostic and potentially predictive value of MET amplification as well as challenges in identifying patient subgroups that may benefit from targeted cancer therapies (Lennerz, J. K. et al., J. Clin. Oncol. 29, 2011, p. 1-8). Currently there are no validated biomarkers to evaluate increased MET copy number, which leads to confusion in the literature about MET amplification and polysomy (Peters, S. et al., Nat. Rev. Clin. Oncol. 9, 314-326 (2012)). Thus, there is a need to identify and treat patients who will most benefit from particular therapies and to provide the most tailored and appropriate therapy to each individual person in need.

SUMMARY

This invention relates to uses of selective MET antagonists for effectively treating cancer patients. In one aspect, the MET antagonist is a selective tyrosine kinase inhibitor. For example, the selective tyrosine kinase inhibitor can be Compound M (6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one) or similar selective tyrosine kinase inhibitor. These compounds and methods of their synthesis are described in U.S. Pat. No. 8,198,448.

The invention provides methods and reagents useful for informing appropriate treatment options using the selective tyrosine kinase inhibitor, and more particularly, Compound M, to treat patients diagnosed with gastric cancer, including but not limited to locally advanced or metastatic gastric or esophagogastric adenocarcinoma are described herein. In another aspect, the invention discloses methods and reagents useful for informing appropriate treatment options using the selective tyrosine kinase inhibitor, and more particularly, Compound M, to treat patients diagnosed with non-small cell lung cancer (NSCLC), for example, adenocarcinoma, squamous cell carcinoma, undifferentiated large cell carcinoma, adenosquamous carcinoma (pleiomorphic carcinoma) and sarcomatoid carcinoma. The methods and reagents described herein are used to provide guidance as to which patients are likely to respond to treatment with the selective tyrosine kinase inhibitor.

In addition, the disclosure provides methods of using MET amplification as predictive biomarkers for determining whether or not a patient diagnosed with cancer will respond to treatment with a selective tyrosine kinase inhibitor such as Compound M.

The invention provides methods of treating a patient diagnosed with cancer, wherein cancer is selected from a group consisting of gastric, colorectal, ovarian, glioblastoma, hepatocellular carcinoma (HCC), biliary tract and NSCLC cancer, wherein a sample of tumor cells obtained from the patient have the presence of focal amplification of the MET gene, the method comprising the step of administering to a patient diagnosed with cancer Compound M effective to provide a therapeutic benefit. In one aspect, focal amplification of the MET gene can be determined by detecting increased MET gene copy number. In another aspect of the invention, the MET gene copy number can be determined by FISH. In a further aspect, the presence of focal amplification of the MET gene can be defined by FISH as a ratio of MET gene copy number to chromosome 7 copy number. The ratio can be 2 or higher, 3 or higher, 4 or higher, or 5 or higher.

The invention provides methods of treating a patient diagnosed with cancer, wherein cancer is selected from a group consisting of gastric, colorectal, ovarian, glioblastoma, HCC, NSCLC and biliary tract cancer, wherein a sample of tumor cells obtained from the patient have the presence of focal amplification of the MET gene, wherein the MET gene copy number is determined by alternative methods including PCR, qPCR, RT-PCR, comparative genomic hybridization or next generation sequencing. In one aspect, the presence of focal amplification of the MET gene is defined by Array Comparative Genomic Hybridization as a ratio of MET gene copy number to a normal diploid genome. In a further aspect, the ratio can be 2.5 or higher.

The invention discloses methods of treating a patient wherein cancer is selected from a group consisting of gastric, colorectal, ovarian, glioblastoma, HCC, NSCLC and biliary tract cancer, wherein a sample of circulating tumor cells obtained from the patient have the presence of high expression of Met protein, the method comprising the step of administering to a patient diagnosed with cancer Compound M effective to provide a therapeutic benefit.

Other methods disclosed herein include the methods of treating a patient diagnosed with cancer, wherein cancer is selected from a group consisting of gastric, colorectal, ovarian, glioblastoma, HCC, biliary tract and NSCLC cancer, wherein a sample of tumor cells obtained from the patient have the presence of high Met protein expression, the method comprising the step of administering to a patient diagnosed with cancer Compound M effective to provide a therapeutic benefit. In one aspect, cancer is hepatocellular carcinoma (HCC).

BRIEF DESCRIPTION OF THE FIGURES

FIG. 7B represents MET amplified MKN45 gastric cancer tumor xenograft model treated with Compound M. Figure shows measurements to day 23. At day 27, vehicle group tumors started to ulcerate, confounding accurate determination of tumor volume. FIG. 7C illustrates MET amplified SNU5 gastric cancer tumor xenograft model treated with Compound M. In FIGS. 7B and 7C arrow indicates the initiation of treatment with Compound M.

DETAILED DESCRIPTION

Figure 1:
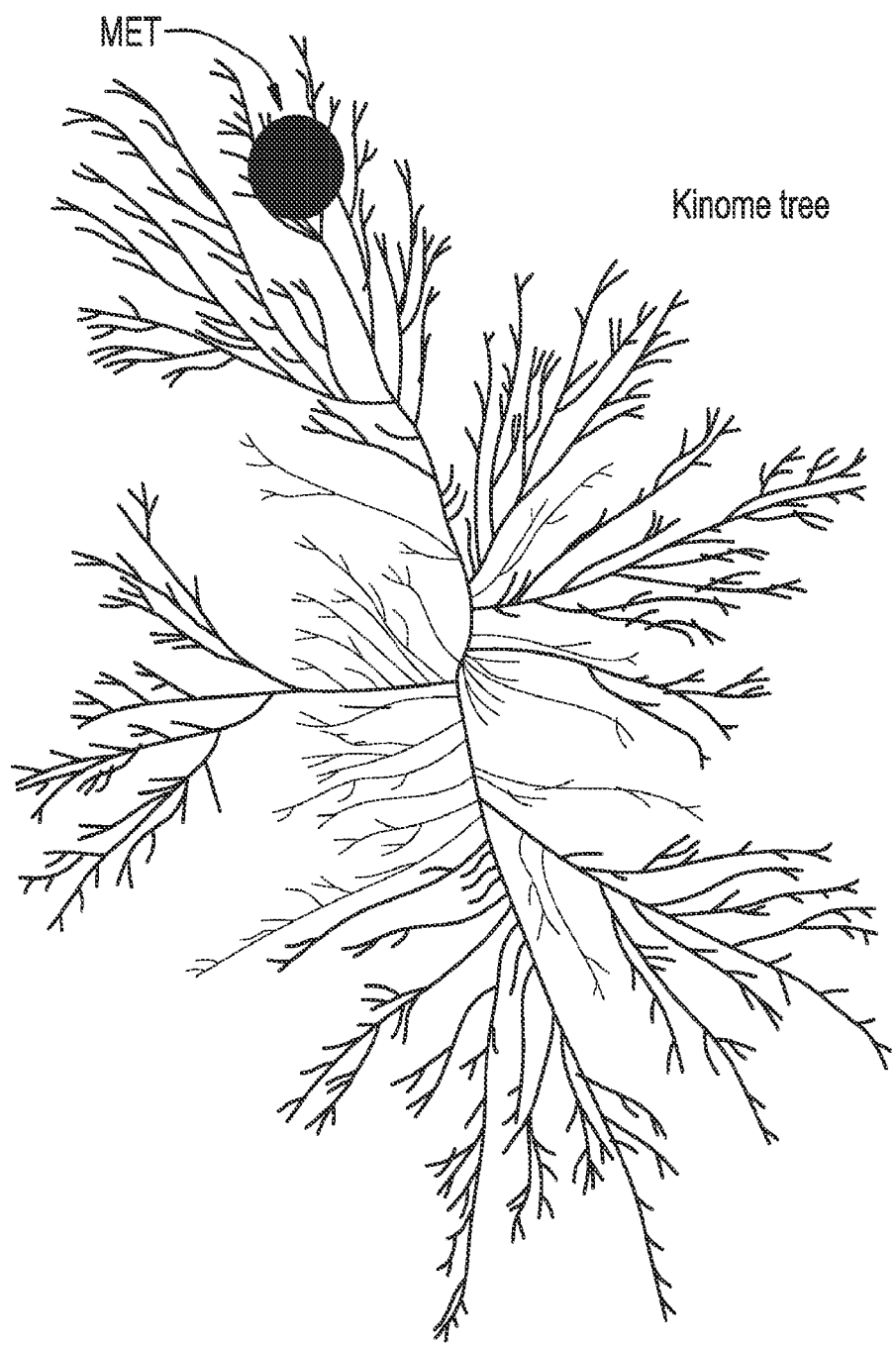
FIG. 1 demonstrates human kinome selectivity profile for Compound M.

All references cited herein, including patents, patent applications, papers, textbooks, and the like, and the references cited therein, to the extent that they are not already, are hereby incorporated herein by reference in their entirety for any purpose. In the event that one or more of the documents incorporated by reference defines a term that contradicts that term's definition in the instant disclosure, this disclosure controls. The section headings used herein are for organizational purposes only and are not to be construed as limiting the subject matter described.

Definitions

As used herein, the term "comprising" indicates the potential inclusion of other agents, elements, steps, or features, in addition to those specified.

In one aspect of the invention, the selective MET inhibitor is 6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one (Compound M).

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

The terms "treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment, or receiving only partial treatment. Those in need of treatment include those already with the condition or disorder as well as those prone to have the condition or disorder or those in which the condition or disorder is to be prevented.

A "previously treated" cancer patient has received prior cancer therapy.

The term "patient" includes human subjects.

The terms "mammal" and "animal" for purposes of treatment refers to any animal classified as a mammal, including humans, domestic and farm animals, and zoo, sports, or pet animals, such as dogs, horses, cats, cows, etc. Preferably, the mammal is human.

The terms, "therapeutic agent" or "pharmaceutical agent", "medicament" or "drug" as used herein refer to a compound or composition capable of inducing a desired therapeutic effect when properly administered to a patient.

The term "effective" and "effectiveness" includes both pharmacological effectiveness and physiological safety. Pharmacological effectiveness refers to the ability of the treatment to result in a desired biological effect in the patient. Physiological safety refers to the level of toxicity or other adverse physiological effects at the cellular, organ and/or organism level (often referred to as side effects) resulting from administration of the treatment. "Less effective" means that the treatment results in a therapeutically significantly lower level of pharmacological effectiveness and/or a therapeutically greater level of adverse physiological effects.

"Therapeutically effective amount" of a therapeutic agent is defined as an amount of the therapeutic agent that is sufficient to show meaningful patient benefit, e.g., to cause a decrease in, amelioration of, or prevention of the symptoms of the condition being treated. For purposes of this invention, meaningful patient benefit includes, but is not limited to, alleviation of symptoms, diminishment of extent of disease, stabilized (e.g., not worsening) state of disease, delay or slowing of disease progression, amelioration or palliation of the disease state, and remission (whether partial or total), whether detectable or undetectable.

"Sample" or "patient sample" refers to a sample from a human, animal, or to a research sample, e.g., cell, tissue, organ, fluid, gas, aerosol, slurry, colloid, or coagulated material. The "sample" may be tested in vivo, e.g., without the removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ or fluid that is processed or stored.

The term "disease state" refers to a physiological state of a cell or of a whole mammal in which an interruption, cessation, or disorder of cellular or body functions, systems, or organs has occurred.

"Cancer" refers to the presence of cells possessing characteristics typical of cancer-causing cells, such as uncontrolled proliferation, immortality, metastatic potential, rapid growth and proliferation rate, and certain characteristic morphological features. Cancer cells may exist alone, or may be a non-tumorigenic cancer cell, such as leukemia cell. In some circumstances cancer cells may be in the form of the tumor, such cells may exist locally or circulate in the bloodstream as independent cells, for example, leukemia cells.

"Gastric cancer" (also known as stomach cancer) is a disease in which the cells forming the inner lining of the stomach become abnormal and start to divide uncontrollably forming a mass called a tumor. The term "gastric cancer" as used herein is an umbrella term and includes, but is not limited to gastric, esophageal, gastroesophageal, locally advanced and metastatic gastric and esophagogastric adenocarcinoma, squamous cell carcinoma, lymphomas, gastrointestinal stromal tumors, and carcinoid tumors.

NSCLC or "non small cell lung carcinoma" refers to a group of diseases including but not limited to squamous cell lung carcinoma (SCC), adenocarcinoma of the lung, large cell lung carcinoma and pulmonary pleomorphic carcinoma.

"Colorectal cancer" refers to colon cancer, rectal cancer or large intestinal cancer and includes adenocarcinoma and squamous cell carcinoma.

"Ovarian cancer" includes surface epithelial-stromal tumor also known as ovarian epithelial carcinoma, which in turn includes serous tumor, endometrioid tumor, and mucinous cystadenocarcinoma; Brenner tumor, transitional cell carcinoma of the ovary, sex cord-stromal tumor, including estrogen-producing granulosa cell tumor and virilizing Sertoli-Leydig cell tumor or arrhenoblastoma; germ cell tumor; as well as mixed tumors.

"Glioblastoma" or glioblastoma multiforme, includes the "classical" subtype carry extra copies of the epidermal growth factor receptor (EGFR) gene, the proneural subtype and mesenchymal subtype.

"Biliary tract cancer" or BTC includes a spectrum of adenocarcinomas encompassing cholangiocarcinoma (CC), which refers to cancers arising in the intrahepatic, perihilar, or distal biliary tree, and gallbladder carcinoma. Tumors occurring in the bile ducts within the liver are referred to as intrahepatic, those occurring in the ducts outside the liver are extrahepatic, and tumors occurring at the site where the bile ducts exit the liver are referred to as perihilar. BTC further includes Klatskin tumor, cholangiocarcinoma occurring at the junction where the left and right hepatic ducts meet to form the common bile duct. BTCs include adenocarcinomas and carcinomas.

"Hepatocellular carcinoma" or HCC refers to a malignant tumor of the liver that develops in the setting of chronic liver disease or cirrhosis, derived from hepatocytes that are transformed into adenocarcinoma.

"Refractory" cancer is the cancer that progresses even though an antitumor agent is being administered to the cancer patient.

"Biomarker" as used herein is defined as an objectively measured indicator of biological processes or response to a therapeutic intervention and can refer to a molecule, such as a gene, mRNA, protein, glycolipid etc., the expression of which in or on a tissue or cell can be detected by known methods and is predictive or can be used to aid prediction for a cell, tissue, or patient's responsiveness to treatment regimes. The biomarker contemplated by the present disclosure is MET gene. In one aspect, the MET biomarker refers to amplification of MET gene, e.g., an average in a population of cells of 2 or more copies of MET gene.

An "effective response" of a patient or a patient's "responsiveness" to treatment or "responsive" as used herein means that a patient or tumor shows a complete response or a partial response after administering an agent, according to RECIST (Response Evaluation Criteria in Solid Tumors). The term "nonresponsive" as used herein means that a patient or tumor shows stable disease or progressive disease after administering an agent, according to RECIST. RECIST is described, e.g., in Therasse et al., February 2000, "New Guidelines to Evaluate the Response to Treatment in Solid Tumors," J. Natl. Cancer Inst. 92(3): 205-216. In one aspect, an effective response means that the clinical or therapeutic benefit imparted to a patient at risk for, or suffering from cancer upon administration of the cancer medicament, contemplated by the present invention, for example, Compound M. Such benefit includes any of the following: extending survival (including overall survival and progression free survival); resulting in an objective response (including a complete response or a partial response); or improving signs or symptoms of cancer.

"Survival," as used herein, refers to the patient remaining alive, and includes overall survival as well as progression free survival. "Progression free survival" or PFS contemplates the patient remaining alive without the cancer progressing or getting worse. "Overall survival" or OS refers to the patient remaining alive for a defined period of time, e.g., one year, five years, etc. from the time of diagnosis of treatment.

By "extending survival" it is understood increasing OS or PFS in a treated patient relative to an untreated patient (a patient not treated with the medicament) or relative to a patient who does not express a biomarker at the designated level, and/or relative to a patient treated with an approved anti-tumor agent.

An "objective response" or OR refers to a measurable response, including complete response or CR or partial response or PR.

"Complete response" or CR as used herein refers to disappearance of all signs of cancer in response to treatment. This does not always mean that the cancer has been cured.

"Partial response" means a decrease in the size of one or more tumors or lesions, or in extent of cancer in the body, in response to treatment.

"C-Met protein" or "Met protein" (also known as c-Met receptor or HGF receptor ("HGFr")) refers to a high affinity tyrosine kinase receptor for HGF expressed on the cell surface of a variety of normal cells and primary solid tumours and in their metastases. C-Met protein is a disulfide-linked heterodimer made of 45 kDa alpha-subunits and 145 kDa beta-subunits. The nucleic acid sequence of the polynucleotide encoding the full length protein of MET was published by Park et al. (Proc. Natl. Acad. Sci. USA 84: 6379-83 (1987) and submitted to GenBank under the accession number NM 000245 or NCBI reference sequence NG_008996.1.

The terms "mutant K-ras polypeptide" and "mutant K-ras protein" are used interchangeably, and refer to a K-ras polypeptide comprising at least one K-ras mutation selected from G13D, G13C, G12V, G12S, G12R, G12D, G12C, and G12A. Certain exemplary mutant K-ras polypeptides include, but are not limited to, allelic variants, splice variants, derivative variants, substitution variants, deletion variants, and/or insertion variants, fusion polypeptides, orthologs, and interspecies homologs. In certain embodiments, a mutant K-ras polypeptide includes additional residues at the C- or N-terminus, such as, but not limited to, leader sequence residues, targeting residues, amino terminal methionine residues, lysine residues, tag residues and/or fusion protein residues. The terms "mutant K-ras polynucleotide", "mutant K-ras oligonucleotide," and "mutant K-ras nucleic acid" are used interchangeably, and refer to a polynucleotide encoding a K-ras polypeptide comprising at least one K-ras mutation selected from G13D, G13C, G12V, G12S, G12R, G12D, G12C, and G12A. The GenBank accession numbers for the nucleic acid sequence of the polynucleotide encoding the full length protein of K-ras is NM_004985.

"Gene amplification" refers to a process by which multiple copies of a gene or gene fragment are formed in a particular cell or cell line. The duplicated region (a stretch of amplified DNA) is often referred to as "amplicon." MET amplification refers to amplification of MET gene.

The "copy number of a gene" refers to the number of DNA sequences in a cell encoding a particular gene product. Generally, for a given gene, a patient has two copies of each gene. The copy number can be increased by gene amplification or reduced by deletion.

A "copy number gain" means determining a multiplication of the entire or a portion of the genome regions.

"Focal amplification" or "focal gene amplification" refers to a state in which cell nuclei express multiple copies of a specific gene above the average chromosome copy number. In another aspect, Focal amplification of MET is an increase in the copy number of MET involving a genomic region shorter than the q arm of chromosome 7, excluding polysomy and whole q arm amplification.

Polysomy refers to the state of a cell nucleus in which a specific chromosome or multiple chromosomes are represented more than twice.

In one aspect, a positive value for MET gene amplification (i.e., MET gene is amplified or MET gene amplification is present in a tumor sample) is defined as a fluorescent in situ hybridization (FISH) result of more than 5 MET gene copies per nucleus. In another aspect, MET amplification is defined as a FISH ratio (ratio of MET gene signals to chromosome 7 signals) of greater than or equal to 2. In a further aspect, MET amplification is considered positive when 10% or more nuclei have at least 15 MET gene copies.

In another aspect, a positive value for MET gene amplification (i.e., MET gene is amplified or MET gene amplification is present in a tumor sample) is defined as a MET log 2 ratio >2.5 using a CGH microarray.

Circulating tumor cells (CTCs) refer to cells that have shed into the vasculature from a primary tumor and circulate in the bloodstream. CTCs thus constitute seeds for subsequent growth of additional tumors (metastasis) in vital distant organs, triggering a mechanism that is responsible for the vast majority of cancer-related deaths. CTCs could be considered a "liquid biopsy" which reveals metastasis in action, providing information about the patient's disease status. While analysis of solid tumors requires invasive procedures that may limit patient compliance, blood tests are easy and safe to perform and multiple samples can be taken over time.

CTCs can be divided in the following types: (1) traditional CTCs are confirmed cancers cells with viable nuclei expressing cytokeratins which demonstrate epithelial origin; have an absence of CD45, indicating the cells are not of hematopoietic origin; and are often larger cells with irregular shape or subcellular morphology; (2) Cytokeratin negative (CK−) CTCs are cancer stem cells or cells undergoing epithelial-mesenchymal transition (EMT), may be the most resistant and most prone to metastasis; express neither cytokeratins nor CD45; have morphology similar to a cancer cell; and importantly have gene or protein expression or genomics associated with cancer; (3) Apoptotic CTCs are traditional CTCs that are undergoing apoptosis (measuring the ratio of traditional CTC to apoptotic CTCs—from baseline to therapy—provides clues to a therapy's efficacy in targeting and killing cancer cells); (4) Small CTCs are cytokeratin positive and CD45 negative, but with sizes and shapes similar to white blood cells. Small CTCs have cancer-specific biomarkers that identify them as CTCs, they have been implicated in progressive disease and differentiation into small cell carcinomas, which often require a different therapeutic course; (5) CTC Clusters are two or more individual CTCs bound together, they may contain traditional, small or CK− CTCs. These clusters have cancer-specific biomarkers that identify them as CTCs. These clusters are associated with increased metastatic risk and poor prognosis.

General Methods

Methods for obtaining biological samples are well known in the art and any standard methods for obtaining biological samples can be employed. Biological samples that find use with the methods of the present invention include but are not limited to serum, blood, plasma, whole blood and derivatives thereof, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy. (See, e.g., Clinical Proteomics: Methods and Protocols, Vol. 428 in Methods in Molecular Biology, Ed. Antonia Vlahou (2008)).

Methods of determining the copy number of a particular genomic region are well known in the art and include hybridization and amplification based assays. According to the methods of the invention, gene copy number may be identified using copy number profiling, such as comparative genomic hybridization (CGH) (including both dual channel hybridization profiling and single channel hybridization profiling (e.g. SNP-CGH)). Other suitable methods including fluorescent in situ hybridization (FISH), PCR, nucleic acid sequencing, and Southern blot analysis may be used in accordance with the invention.

In some aspects of the invention, the gene copy number is identified using CGH. In comparative genomic hybridization methods, a "test" collection of nucleic acids (e.g. from a tumor or cancerous cells) is labeled with a first label, while a second collection (e.g. from a normal cell or tissue) is labeled with a second label. The ratio of hybridization of the nucleic acids is determined by the ratio of the first and second labels binding to each probe in an array. Differences in the ratio of the signals from the two labels, for example, due to gene amplification in the test collection, are detected and the ratio provides a measure of the gene copy number, corresponding to the specific probe used. A cytogenetic representation of gene copy-number variation can be generated by CGH, which provides fluorescence ratios along the length of chromosomes from differentially labeled test and reference genomic DNAs.

In some aspects of the present invention, the gene copy number is analyzed by microarray based CGH (array-CGH), which offers high resolution. For example, the traditional CGH generally has a 20 Mb limited mapping resolution, whereas in microarray based CGH, the fluorescence ratios of the differentially labeled test and reference genomic DNAs provide a locus-by-locus measure of DNA copy-number variation, thereby achieving increased mapping resolution. Details of various microarray methods can be found in the literature, for example, U.S. Pat. No. 6,232,068; Pollack et al., Nat. Genet., 23(1):41-6, (1999), Pastinen (1997) Genome Res. 7: 606614; Jackson (1996) Nature Biotechnology 14:1685; Chee (1995) Science 274: 610; WO 96/17958, Pinkel et al. (1998) Nature Genetics 20: 207-211 and others. High resolution CGH arrays can be performed using the Agilent, Affymetrix, or Illumina platforms. The DNA used to prepare the CGH arrays is not critical. For example, the arrays can include genomic DNA, e.g., overlapping clones that provide a high resolution scan of the portion of the genome of interest.

The starting amount of DNA required for the assays may be reduced through use of a nucleic acid amplification system that multiplies the target nucleic acid being detected. Examples of such systems include the polymerase chain reaction (PCR) system and the ligase chain reaction (LCR) system. Other suitable methods include are the nucleic acid sequence based amplification (NASBAO, Cangene, Mississauga, Ontario) and Q Beta Replicase systems. In one aspect of the invention, the gene copy number alterations in a genome are determined by single channel profiling, such as single nucleotide polymorphism (SNP)-CGH. Traditional CGH data consists of two channel intensity data corresponding to the two alleles. The comparison of normalized intensities between a reference and subject sample is the foundation of traditional array-CGH. Single channel profiling (such as SNP-CGH) is different in that a combination of two genotyping parameters is analyzed: normalized intensity measurement and allelic ratio. Collectively, these parameters provide a more sensitive and precise profile of chromosomal aberrations. SNP-CGH also provides genetic information (haplotypes) of the locus undergoing aberration. In one aspect, the disclosure contemplates using NanoString direct DNA and/or mRNA quantification is used to determine the copy number gain (Nat Biotechnol. 2008 March; 26(3):293-4). Unlike other platforms, NanoString technology is able to assay nucleic acids from FFPE samples, and also allows measurement of average copy number gain per genome.

The invention provides other methods for determining the gene copy number alterations in a genome, for example, fluorescence in situ hybridization (FISH), which is well known to those of skill in the art (Angerer, 1987 Meth. Enzymol. 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes used in such applications are typically labeled, for example, with radioisotopes or fluorescent reporters. In one aspect, probes are sufficiently long, for example, from about 50, 100, or 200 nucleotides to about 1000 or more nucleotides, to enable specific hybridization with the target nucleic acid(s) under stringent conditions.

In some applications it is necessary to block the hybridization capacity of repetitive sequences. Thus, in some embodiments, tRNA, human genomic DNA, or Cot-1 DNA is used to block non-specific hybridization.

In another aspect of the invention, Southern blotting can be used to determine the gene copy number alterations in a genome. Methods for doing Southern blotting are known to those of skill in the art (see Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, N Y, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., genomic DNA from the same or related cell, tissue, organ, etc.) provides an estimate of the relative copy number of the target nucleic acid.

In a further aspect of the invention, amplification-based assays, such as PCR, are used to determine the gene copy number alterations in a genome. In such amplification-based assays, the genomic region where a copy number alteration occurred serves as a template in an amplification reaction. In a quantitative amplification, the amount of amplification product will be proportional to the amount of template in the original sample. Comparison to appropriate controls provides a measure of the copy number of the genomic region. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y.

Real time PCR can be used in the methods of the invention to determine gene copy number alterations. (See, e.g., Gibson et al., Genome Research 6:995-1001, 1996; Heid et al., Genome Research 6:986-994, 1996). Real-time PCR evaluates the level of PCR product accumulation during amplification. To measure DNA copy number, total genomic DNA is isolated from a sample. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of skill in the art, and control (for example, beta-actin) primers and probes may be obtained commercially from, e.g., Perkin Elmer/Applied Biosystems (Foster City, Calif.). To quantify the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, for example, for RNA in: Gibson et al., 1996, Genome Res., 10:995-1001; and for DNA in: Heid et al., 1996, Genome Res., 10:986-994.

A TaqMan-based assay also can be used to quantify a particular genomic region for gene copy number alterations. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, www.perkinelmer.com).

Other suitable amplification methods include ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc. In one aspect, DNA sequencing is used to determine the gene copy number alterations in a genome. Methods for DNA sequencing are known to those of skill in the art.

The invention provides methods such as karyotyping (e.g., spectral karyotyping, SKY) to determine the chromosomal structural aberrations in a genome. Methods for karyotyping are known to those of skill in the art. For example, for SKY, a collection of DNA probes, each complementary to a unique region of one chromosome, may be prepared and labeled with a fluorescent color that is designated for a specific chromosome. DNA amplification, translocations or other structural abnormalities may be determined based on fluorescence emission of the probes.

Gene copy number gain is sometimes associated with a mutation leading to increased levels of mRNA, protein expression or activity. In some aspects, gene copy number can be determined by quantifying the increase in the levels of mRNA or protein expression and activity. mRNA levels can be measured using methods well known in the art, such as Northern blot analysis, and real time PCR. Protein levels can be measured using standard protein assays, using immunologic-based assays (such as ELISAs, IHC and related techniques), or using activity assays.

Certain methods of detecting a mutation in a polynucleotide are known in the art. Such exemplary such methods include, but are not limited to, sequencing, primer extension reactions, electrophoresis, picogreen assays, oligonucleotide ligation assays, hybridization assays, TaqMan assays, SNPlex assays, and assays described, e.g., in U.S. Pat. Nos. 5,470,705, 5,514,543, 5,580,732, 5,624,800, 5,807,682, 6,759,202, 6,756,204, 6,734,296, 6,395,486, and U.S. Patent Publication No. US 2003-0190646.

In some aspects, detecting a mutation in a polynucleotide comprises first amplifying a polynucleotide that may comprise the mutation. These methods for amplifying a polynucleotide are known in the art. Such amplification products may be used in any of the methods described herein, or known in the art, for detecting a mutation in a polynucleotide. Other exemplary methods include, but are not limited to, detecting using a specific binding agent specific for the mutant polypeptide. Other methods of detecting a mutant polypeptide include, but are not limited to, electrophoresis and peptide sequencing. Methods of detecting a mutation in a polynucleotide and/or a polypeptide are described, e.g., in Schimanski et al. (1999) Cancer Res., 59: 5169-5175; Nagasaka et al. (2004) J. Clin. Oncol., 22: 4584-4596; PCT Publication No. WO 2007/001868 A1; U.S. Patent Publication No. 2005/0272083 A1; and Lievre et al. (2006) Cancer Res. 66: 3992-3994.

Methods for determining Met expression levels are known in the art. In one aspect, Met protein levels can be assessed by immunochemistry (IHC, Dako). High Met expression was defined as the presence of any tumor cells with membrane staining at 3+ intensity.

In one aspect, microarrays comprising one or more polynucleotides encoding one or more mutant K-ras polypeptides can be used. In other aspects, microarrays comprising one or more polynucleotides complementary to one or more polynucleotides encoding one or more mutant K-ras polypeptides can be employed. In a further aspect, the presence or absence of one or more mutant K-ras polynucleotides in two or more cell or tissue samples is assessed using microarray technology. In certain aspects, the quantity of one or more mutant K-ras polynucleotides in two or more cell or tissue samples is assessed using microarray technology.

In one aspect, the presence or absence of one or more mutant K-ras polypeptides in two or more cell or tissue samples is assessed using microarray technology. In one example, mRNA is first extracted from a cell or tissue sample and is subsequently converted to cDNA, which is hybridized to the microarray. The presence or absence of cDNA that is specifically bound to the microarray can be indicative of the presence or absence of the mutant K-ras polypeptide. The expression level of the one or more mutant K-ras polypeptides can be assessed by quantitating the amount of cDNA that is specifically bound to the microarray.

In other aspects of the invention, microarrays comprising one or more specific binding agents to one or more mutant K-ras polypeptides are provided. For example, the presence or absence of one or more mutant K-ras polypeptides in a cell or tissue can be assessed. In certain such aspects, the quantity of one or more mutant K-ras polypeptides in a cell or tissue can be assessed.

Methods of detecting CTCs are known in the art. The detection of CTCs may have important prognostic and therapeutic implications. However, due to their low numbers, the detection is very challenging. It is estimated that CTCs are found in frequencies of 1-10 CTC per mL of whole blood in patients with metastatic disease. Approximately 0.01% of the cells that have detached from the primary tumor can form metastasis. Thus, the challenges of understanding CTCs biological properties are associated with isolating 1 CTC per mL of blood, either by enrichment, or with enrichment-free assays that identify all CTC subtypes in sufficiently high definition to satisfy diagnostic pathology image-quantity requirements in patients with a variety of cancer types. In one example, CTCs can be captured from the vasculature by using specific antibodies able to recognize specific tumoral marker (e.g., EpCAM, an epithelial cell adhesion molecule). This approach, however, requires a sufficient expression of the selected protein on the cell surface, event necessary for the enrichment step. Since EpCAM and other proteins (e.g., cytokeratins) are not expressed in some tumors and can be done regulated during the epithelial to mesenchymal transition, other methods require new enrichment strategies. In one aspect, enumeration of CTC in whole blood can be done by the CellSearch system. Clinical testing done with this method demonstrated that presence of CTC is a strong prognostic factor for overall survival in patients with metastatic breast, colorectal or prostatic cancer.

Any useful method for isolation of CTCs must allow (i) their identification and enumeration and (ii) their characterization through immunocytochemistry, fluorescence in situ hybridization (FISH) DNA and RNA assays, and all other relevant molecular techniques using DNA and RNA. When circulating tumor cells are captured from blood using filtration devices (such as ScreenCell isolation device), further morphological and molecular characterization is required to reveal important predictive information and report changes in CTC biology, for example during tumor relapse. ViewRNA assay for CTCs characterization is the only in situ hybridization technology that allows multiplex, single-molecule RNA detection of any RNA target. The exceptional sensitivity and specificity is achieved by using proprietary probe design, simultaneous branched DNA (bDNA) signal amplification and background suppression.

CellSearch method is based on the use of iron nanoparticles coated with a polymer layer carrying biotin analogues and conjugated with antibodies anti EpCAM for capturing CTCs, and on the use of an analyzer to take images of isolated cells upon their staining with specific fluorescent antibody conjugates. Blood is sampled in an EDTA tube with an added preservative. Upon arrival in the lab, 7.5 mL of blood is centrifuged and placed in a preparation system. This system first enriches the tumor cells immunomagnetically by means of ferrofluid nano-particles and a magnet. Subsequently recovered cells are permeabilized and stained with a nuclear stain, a fluorescent antibody conjugate against CD45 (leukocyte marker), and cytokeratin 8, 18 and 19 (CKs). The sample is then scanned on an analyzer which takes images of the nuclear, cytokeratin, and CD45 stains. To be considered a CTC a cell must contain a nucleus, be positive for cytoplasmic expression of cytokeratin as well as negative for the expression of CD45 marker, and have a diameter larger than 5 μm. If the total number of tumor cells found to meet the criteria cited above is 5 or more, a blood sample is positive. In studies done on prostate, breast and colon cancer patients, median survival of metastatic patients with positive samples is about half the median survival of metastatic patients with negative samples. This system is characterized by a recovery capacity of 93% and a detection limit of one CTC per 7.5 mL of whole blood. Despite its sensitivity and reproducibility, the CellSearch Method requires specific equipment to perform the analysis.

Epic Sciences method involves technology to separate nucleated cells from red blood cells, which lack a nucleus. In contrast to many other methods, Epic Sciences does not purify the cells or enriches them, but identifies them within the context of the other blood compounds. All nucleated cells, including normal white blood cells and CTCs, are exposed to fluorescent-tagged antibodies specific for cancer biomarkers. In addition, Epic imaging system captures pictures of all the cells on the slide (approximately 3 million), records the precise coordinates of each cell, and analyzes each cell for 90 different parameters, including the fluorescence intensity of the four fluorescent markers and 86 different morphological parameters. CTC count from a subset of slides per sample is extrapolated to calculate the total number of CTCs per patient sample. The remaining unanalyzed slides are stored for future biomarker discovery efforts. Epic can also use FISH and other staining techniques to look for abnormalities such as duplications, deletions, and rearrangements. The imaging and analysis technology also allows for the coordinates of every cell on a slide to be known so that a single cell can be retrieved from the slide for analysis using next-generation sequencing. A hematopathology-trained algorithm incorporates numerous morphology measurements as well as expression from cytokeratin and CD45. The algorithm then proposes candidate CTCs that a trained reader confirms. Cells of interest are analyzed for relevant phenotypic and genotypic markers, with regional white blood cells included as negative controls. Epic molecular assays measure protein expression and also interrogate genomic abnormalities in CTCs for more than 20 different cancer types.

Maintrac is a diagnostic platform applying microscopic methods to identify rare cells in body fluids and their molecular characteristics. For CTCs, an approach based on microscopic identification of circulating tumor cells is used. To prevent damage and loss of the cells during the process, maintrac uses just two steps towards the identification. In contrast to many other methods, maintrac does not purify the cells or enriches them, but identifies them within the context of the other blood compounds. To obtain vital cells and to reduce stress of those cells, blood cells are prepared by only one centrifugation step and erythrocyte lysis. Like Cell-Search maintrac uses an EpCAM antibody. It is, however, not used for enrichment but rather as a fluorescent marker to identify those cells. Together with the nuclear staining with propidium iodide the maintrac method can distinguish between dead and living cells. Only vital, propidium excluding EpCAM positive cells are counted as potential tumor cells. Only living cells can grow into tumors, therefore dying EpCAM positive cells can do no harm. The suspension is analyzed by fluorescence microscopy, which automatically counts the events. Simultaneous event galleries are recorded to verify whether the software found a true living cell and to differentiate between skin epithelial cells for example. Close validation of the method showed that additional antibodies of cytokeratins or CD45 did not have any advantage. Unlike other methods maintrac does not use the single cell count as a prognostic marker, rather maintrac utilizes the dynamics of the cell count. Rising tumor cell numbers are an important factor that tumor activity is ongoing. Decreasing cell counts are a sign for a successful therapy.

Methods of Treating Patients with Gastric, Colorectal, Ovarian, Glioblastoma, HCC and NSCLC Cancer The data provided in the Examples show that the administration of a selective tyrosine kinase inhibitor such as Compound M leads to improved progression-free survival as well as overall survival of the treated disease. More specifically, the data show that the administration of Compound M leads to progression-free survival as well as overall survival of the treated disease. The actual effect appears to be correlated with the amplification level of MET in the tumors to be treated. Therefore, any patient diagnosed with gastric, colorectal, ovarian, glioblastoma, biliary tract and NSCLC cancer, having certain levels of MET in their tumor cells may benefit from the disclosed methods. There is no requirement as to the stage of the patient's tumor; the tumor can be at any stage of growth, for example T2, T3 or T4. The tumor can also exist at any stage of the nodal stage, for example N0, N1, N2a, N2b, N2c or N3. Further, the tumor can be staged as such by any system, for example the AJCC system or the TNM staging system.

Responsiveness or nonresponsiveness to treatment with Compound M can be determined using any established criteria. In a specific example, responsiveness or nonresponsiveness can be determined using the widely adopted RECIST (Response Evaluation Criteria in Solid Tumors) criteria or Macdonald criteria for GBM. See, e.g., Therasse et al., (2000) *J. Natl. Cancer Inst.* 92(3): 205-216, Macdonald D. R. et al. J Clin Oncol. 1990; 8:1277-1280. Complete response and partial response according to RECIST are both considered to be responsive to treatment with Compound M. Stable disease and progressive disease are both considered to be nonresponsive to treatment with Compound M.

As described herein and in more detail in the Examples, it has been determined that patients with gastric, colorectal, ovarian, glioblastoma, biliary tract and NSCLC cancer whose tumors have certain levels of MET amplification will exhibit an enhancement in overall survival when treated with Compound M. Moreover, it has been determined that these patients, whose tumors have certain levels of MET amplification will exhibit an enhancement in overall survival when treated with Compound M. Accordingly, a method of treating such patients is provided. In one aspect of a method of treating a patient with gastric, colorectal, ovarian, glioblastoma, HCC, biliary tract and NSCLC cancer comprises determining the MET amplification level in a patient's tumor sample. As is the case with all of the disclosed methods, in order to make the determination, any convenient method can be employed. For example, techniques as varied as described above can be used. Most often, it will be desirable to obtain a sample of the patient's tumor and perform the determination in an in vitro setting.

In one aspect, the MET amplification level of a tumor sample obtained from a patient diagnosed with cancer can be readily determined using any commercially available kit or a service provider.

The determination of MET amplification level in a sample from a patient with gastric, colorectal, ovarian, glioblastoma, HCC, biliary tract and NSCLC.

The guidelines can be quantitative, semi-quantitative or qualitative. In one aspect, MET copy number can be measured in the nucleus of the tumor cells. (Capuzzo et al., J. Nat. Cancer Inst., Vol. 97, No. 9, 2005: 643-655; Capuzzo et al., Brit. J. of Cancer (2008) 99, 83-89).

As demonstrated by the data presented in the Examples, patients diagnosed with gastric cancer whose tumor samples had certain levels MET amplification and who received therapy comprising Compound M showed an enhancement in progression-free survival and in overall survival. Thus, if the patient diagnosed with gastric cancer has certain levels of MET amplification in their tumor sample, as described above, the patient is predicted to benefit from treatment with a selective MET inhibitor, such as Compound M.

Continuing with the method, if the patient's tumor has certain levels of MET amplification, the patient can be administered Compound M. In certain aspects, the frequency of dosing will take into account the pharmacokinetic parameters of Compound M in the formulation used. For example, a clinician may administer a therapeutically effective dose of Compound M until the desired effect is achieved. In certain embodiments, a therapeutically effective dose of Compound M may be administered as a single dose or as two or more doses (which may or may not contain the same amount of the desired molecule) over time. In one aspect, Compound M can be administered orally in doses 10 mg, 25 mg, 50 mg, 75 mg, 100 mg, 150 mg, 200 mg, 250 mg, 300 mg, 350 mg, 400 mg, 450 mg or 500 mg. Further refinement of the appropriate dosage is routinely made by those of ordinary skill in the art and is within the ambit of tasks routinely performed by them. For example, in one aspect a therapeutically effective dose Compound M comprises an amount of Compound M that increases over the course of a patient treatment. In another example, a therapeutically effective dose of Compound M comprises an amount of Compound M that decreases over the course of a patient treatment.

All of the disclosed methods can be supplemented as desired. For example, the disclosed methods can be supplemented by adjusting the therapy of a patient having colorectal, ovarian, glioblastoma, biliary tract, HCC and NSCLC cancer based on an evaluation of the results of the method. In one aspect, a patient not receiving therapy comprising Compound M can be placed on such a regimen, based on the determination of MET level in the patient's sample of tumor cells.

Method of Predicting Whether a Patient with Gastric, Colorectal, Ovarian, Glioblastoma, Biliary Tract and NSCLC Cancer Will Benefit from Treatment Comprising Compound M The invention also provides methods of predicting whether a patient having gastric, colorectal, ovarian, glioblastoma, biliary tract, HCC or NSCLC cancer will benefit from treatment comprising Compound M. In one aspect the method comprises determining the level of MET amplification in a sample from a patient diagnosed with gastric, colorectal, ovarian, glioblastoma, biliary tract or NSCLC cancer, wherein if the patient's sample has a certain level of MET amplification, the patient is predicted to benefit from treatment with Compound M.

Initially MET amplification is determined from a sample of tumor cells obtained from a patient. In order to make the determination, any convenient method can be employed. For example, techniques as varied as IHC, FISH, qPCR or a mass spectrometry-based approach can be employed. In one aspect, it will be desirable to obtain a sample of the patient's tumor and perform the determination in an in vitro setting.

In one aspect, MET amplification of a tumor sample obtained from a patient can be readily determined using any commercially available kit or a service provider. The determination of MET amplification in a sample from a patient diagnosed with gastric cancer can be made on the basis of standard scoring guidelines. The guidelines can be quantitative, semi-quantitative or qualitative. Standard FISH scoring practices require the identification of 20-40 individual, intact nuclei within a sample. Copy number of the MET gene and the chromosome 7 gene are quantitated for each nuclei and an average copy number per nuclei is calculated to yield a score for an individual sample.

In one aspect of the invention, if the patient diagnosed with gastric, colorectal, ovarian, glioblastoma, biliary tract, HCC or NSCLC cancer has certain levels of MET amplification in their tumor sample, as described above, the patient is predicted to benefit from treatment with Compound M.

In another aspect, in another aspect, if the patient is determined to have a K-ras mutation at either of 'hotspot' codons 12 and 13, e.g. G13D, G13C, G12V, G12S, G12R, G12D, G12C, or G12A, the patient is predicted not to benefit from treatment with Compound M.

In one aspect of the invention, the route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain aspects, the compositions may be administered by bolus injection or continuously by infusion, or by implantation device.

EXAMPLES

The following examples, including the experiments conducted and results achieved are provided for illustrative purpose only and are not to be construed as limiting upon the claims.

Example 1. Materials and Methods

Array Comparative Genomic Hybridization (aCGH)

Genomic DNA samples were prepared for aCGH using the Roche Nimblegen Dual Color Labeling Kit. (Roche Cat#06370250001) according to the manufacturer's instructions. Briefly, 250 ng of normal donor (pool of 40 normal males) or experimental genomic DNA was mixed with either Cy3- or Cy5-labeled random primer solution, incubated at 99° C. for 10 minutes and quick-chilled in an ice/water bath for 2 minutes. Samples were then mixed with dNTPs (to a final concentration of 1 mM) and 100 U Exo-Klenow enzyme in a total reaction volume of 100 μl. Reactions were incubated 2 hours at 37° C., and terminated by addition of kit stop solution. Labeled product was purified using ethanol precipitation and quantified using the Nanodrop ND-1000. (Nanodrop Products, Wilmington, Del.).

Arrays were hybridized following the Oligonucleotide Array-Based CGH for Genomic DNA Analysis, with modifications. Briefly, 20 μg of Cy5-labeled experimental sample was mixed with 20 μg of Cy3-control DNA (pool of 40 normal male donor genomic DNAs), 25 μg Human Cot-1 DNA, Blocking Reagent, and Hybridization Buffer. Hybridization cocktails were incubated at 99° C. for 3 minutes, then held at 37° C. for 30 minutes. Following incubation, samples were hybridized against the SurePrint G3 Human CGH Microarray 2×400K (Agilent Technologies, Santa Clara, Calif.) for 40 hours at 65° C., rotating at 20 rpm. Samples were washed according to the manufacturer's Wash Procedure A and scanned at 3 μm using 100% PMT for Cy3 and 50% PMT for Cy5 on a DNA Microarray Scanner Model G2505C (Agilent Technologies, Santa Clara, Calif.). Scanned data was feature extracted using Agilent Feature Extraction v10, and .txt files were imported into ArrayStudio (OmicSoft, Cary, N.C.) software to calculate the log 2 ratio of Cy5 signal intensity to Cy3 signal intensity. Log 2 ratio is then used to identify genomic regions of differential copy number, as any non-zero log 2 ratio suggests a different copy number from the pooled normal control genomic DNA.

Next-Generation Sequencing

Genomic DNA was assayed for mutational status using the Ion Torrent Ampliseq 2.0 kit with the Cancer Hotspots Panel v2, using 10 ng genomic DNA, according to the manufacturer's instructions. (Life Technologies, Cat#4475345 and 4475346) Equalized libraries were templated onto Ion Sphere Particles (ISPs) using the Ion PGM Template OT2 200 Kit (Cat#4480974). Templated ISPs were quantified using the Ion Sphere Quality Control Kit (Cat#4468656) and sequenced on the Ion Torrent PGM using the Ion PGM Sequencing 200 Kit v2 (Cat#4482006).

Ion Torrent Suite 3.6.2 was used for base-calling, alignment and variant calling, using parameters set to Somatic Mutation, High Stringency (Ion Ampliseq Library Preparation (MAN0006735_Rev5); Ion PGM™ Template OT2 200

Kit (MAN0007220_Rev4); Ion PGM™ Sequencing 200 Kit v2 (MAN0007273_Rev1) and Torrent Suite™ Software 3.6.2 (July 2013).

Human Kinome Active Site-Directed Competition Binding Assay

The KINOME scan screening platform, which utilizes an active site-directed competition binding assay, was used to quantitatively measure interactions between Compound M and 402 kinases (Davis et al, 2011. Nat. Biotechnol. Vol. 29, pp. 1046-1057).

For most kinase assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µm non-biotinylated affinity ligand) and incubated at room temperature with shaking for 30 minutes. The kinase concentration in the eluates was measured by qPCR as described in as described in Fabian et al. Nat. Biotechnol. 23, 329-336 (2005).

Results from the human kinome active site binding assay were reported as percent of control (% Ctrl) or percentage of qPCR signal (bound kinase) obtained in the presence of 1 µM Compound M relative to the signal obtained with DMSO only. Smaller % Ctrl values reflect greater affinity for the kinase of interest.

% Ctrl Calculation $$((\text{test compound signal} - \text{positive control signal})/(\text{negative control signal} - \text{positive control signal}))*100$$

where:
test compound=Compound M
negative control=DMSO (100% Ctrl)
positive control=control compound (0% Ctrl)

FISH Assay Using MET/CEN-7 IQFISH Dako Probe Mix Code Y5217—Gastric and Esophageal Cancer The copy number of MET was determined by direct fluorescence in situ hybridization (FISH) using MET/CEN-7 IQFISH Probe Mix which detects the copy number of the MET gene located on chromosome 7q31.2 using the chromosome 7 centromer region as a reference. The specific hybridization to the two target results in formation of a distinct red fluorescent signal at each MET gene and a distinct green fluorescent signal at each centromeric region of chromosome 7, wherein the Texas Red-labeled DNA probe (MET) binds to a 269 kb segment containing the MET gene on chromosome 7q31.2 and the fluorescein-labeled PNA probe (CEN-7) binds to the centromeric region of chromosome 7.

Specimen were prepared as follows. Formalin-fixed paraffin-embedded (FFPE) adenocarcinoma specimens of gastric, gastroesophageal junction or esophageal origin from biopsies, excisions or resection were handled to preserve the tissue for FISH analysis. Standard methods of tissue processing for immunocytochemical staining were used for all specimens. MET/CEN-7 IQFISH Probe Mix, Code Y5217 (based on a combination of PNA (peptide nucleic acid) and DNA technology), supplied in IQFISH hybridization buffer which do not require blocking reagent, together with Histology FISH Accessory Kit, Code K5799, was used according to the staining protocol B.3.a of K5799, Section B.3.a: Staining protocol for FISH probes diluted in ethylene carbonate-based hybridization buffer.

Quality control was conducted as follows. Normal cells were allowed for an internal control of the staining run and were evaluated using 20× and 40× objective. Normal cells with 1-2 clearly visible green signals indicate that the CEN-7 PNA Probe has successfully hybridized to the centromeric region of chromosome 7. Normal cells having 1-2 clearly visible red signals indicate that the MET DNA Probe has successfully hybridized to the MET amplicon. Due to tissue sectioning, some normal cells had less than the expected 2 signals of each color. Failure to detect signals in normal cells indicated assay failure, and such results were considered invalid.

Accessible Tissue.

Only cells in the invasive component of the tumor were counted. In cases with intestinal metaplasia and adenocarcinoma in the same specimen, only the adenocarcinoma component was scored. Areas of heavy inflammation, necrosis and areas where the nuclear borders were ambiguous (including overlapping nuclei) were avoided. Nuclei requiring subjective judgment or with weak signal intensity and non-specific or high background were not included.

The complete FISH stained sections were evaluated using a microscope. The tumor within the context of the H&E stained slide was located and the same area was evaluated on the FISH stained slide. Before enumeration of the FISH stained slide, the overall signal distribution (homogenous and heterogenous) on the signal enumeration sheet was noted. In case of heterogeneous distribution it was noted whether focal amplification or single cell amplification (mosaic) was present. If the signal distribution was homogenous, the number of chromosome centromers (green signals) and the number of MET genes (red signals) were enumerated, respectively, from a total of 20 cells in 2 representative tumor areas. In case of heterogenous signal distribution a total of 20 cells from selected areas were enumerated as specified: (A) If focal amplification existed, areas with amplified cells were selected; (B) if mosaic distribution or amplified, polysomal and disomal cells were present, count was done in areas with amplified cells, Within these areas, not only the amplified cells but also the adjacent non-amplified cells were counted for a total of 20 cells, trying not to select overlapping areas and disregarding staining of bacterial DNA. A number of specialized cells (mast cells and macrophages), interspersed in the gastric tissue, exhibited a high level of staining by the MET probe due to presence of bacterial DNA, resulting in highly red fluorescent cells that are clearly distinct from tumor cells with high MET amplification. When in doubt, staining was checked using the monofilters as this unspecific staining was visible using both Texas Red and FITC monofilters. The signals derived from individual nuclei were evaluated using a DAPI filter.

Signal Enumeration.

In the areas selected for signal evaluation, the analysis began in the upper left quadrant of the selected areas, scanning from left to right, one of the 20 adjacent nuclei were chosen and then counted in a cell-by-cell fashion, only leaving out the nuclei that did not meet the quality criteria. The number of signals within the nuclear boundary of each evaluated nucleus was counted according to the following guidelines: (a) focus up and down to find all of the signals in the individual nucleus; (b) count two signals that were the same size and separated by a distance equal to or less than the diameter of the signal as only one signal. The distance had to be at least equal to the diameter of one normal-size signal in order to count two individual signals. When the distance between two signals was less than the diameter of a signal it was counted as one. In nuclei with high levels of MET amplification, the MET signals sometimes were positioned very close to each other forming a cluster of signals, in which case the number of MET signals could not be counted, but were estimated. Special attention was paid to the green signal, as clusters of red MET signals could cover the green signals making them impossible to see. In case of doubt, the green signals were checked using a specific FITS filter.

Nuclei without signals or with signal of only one color were not scored. Only those nuclei with one or more FISH signals of each color were scored, and counts were recorded, counting 20 nuclei per tissue specimen from at least two distinct tumor areas. The MET/CEN-7 ratio was calculated by dividing the total number of red MET signals by the total number of green CEN-7 signals. Specimens with a MET/CEN-7 ratio above or equal to 2 were considered MET gene amplified. Results at or near the cut-off (1.8-2.2) were interpreted with caution. If the ratio was equivocal (1.8-2.2), an additional 20 nuclei were counted and the ratio for the total 40 nuclei was calculated. In cases of doubt, the specimen slide was re-scored.

FISH Assay Using MET/CEN-7 IQFISH Dako Probe Mix Code Y5217—Non-Small Cell Lung Cancer Analysis was conducted as described above using the same probes and reagents. Specimen preparation was done as follows. Formalin-fixed paraffin-embedded (FFPE) specimens of non-small cell lung cancer (NSCLC) origin from biopsies, excisions or recessions were handled to preserve the tissue for FISH analysis. Standard methods of tissue processing for immunocytochemical staining were used for all specimens.

Cancer Cell Lines

Human cancer cell lines were purchased from ATCC, JCRB, Sigma Aldrich or DSMZ. All cell lines were propagated in growth media per the suppliers' recommendation and maintained in 5% $CO_2$ and 37° C.

Cancer Cell Line Viability Assay

Cancer cell line viability assays were carried out using the CellTiter-Glo Luminescent Cell Viability Assay from Promega (Madison, Wis.). Optimal cell seeding densities were determined using time lapse imaging to maximize signal window and ensure cells were not contact growth inhibited at the 72 hour time point. Cells were seeded in 96 well plates in complete growth media and allowed to adhere to the bottom of the plate by incubation at 37° C. and 5% $CO_2$ overnight. Cells were then treated with a 10-step serial dilution of Compound M and DMSO control in complete growth media. Plates were incubated at 37° C. and 5% $CO_2$ for 72 hours. Treated plates were then allowed to equilibrate to room temperature along with, CellTiter-Glo substrate and buffer solution prior to use in the viability assay. CellTiter-Glo substrate vials were reconstituted in 10 mL of buffer solution and added to assay plates in 100 μL/well volumes. Plates were shaken for 2 minutes at 700 rotations per minute with an orbit diameter of 3 mm followed by room temperature incubation for 10 minutes. Plates were then read using an Envision plate reader on luminescent setting.

To calculate growth inhibition effects (0-200% scale), time zero vehicle treated wells ($V_0$), were read at the time of compound addition for each cell line. Together with 72 hour Compound M treated ($T_{72}$) and DMSO treated wells ($V_{72}$) the following equations were used:

Growth Inhibition Equations:

If $T_{72} < V_0$:

$$\text{Growth Inhibition} = 100*(1-(T_{72}-V_0)/V_0)$$

If $T_{72} < V_0$:

$$\text{Growth Inhibition} = 100*(1-(T_{72}-V_0)/(V_{72}-V_0))$$

SDS-PAGE and Immunoblotting

Cells were seeded in 10 cm dishes at varying densities and allowed to adhere by incubating at 37° C. and 5% $CO_2$ overnight. Cells were treated with Compound M at indicated doses or DMSO for 2 or 24 hours. Cells were harvested in 250 μL lysis buffer containing protease and phosphatase inhibitors. For suspension cell lines, cells were pelleted prior to lysis buffer addition. Protein concentrations for individual lysates were measured using a BCA protein assay. 25 μg of protein lysate per sample was resolved on Life Technologies (Carlsbad, Calif.) NuPAGE Bis-Tris gels per manufacturer's. Samples were transferred to nitrocellulose membranes for Western blot analysis. Membranes were blocked in 5% milk prepared in TBST for 1 hour at room temperature. Total and phospho-specific antibodies for specified endpoints were used at 1:1000 dilutions in 5% milk/TBST (total) or 5% BSA/TBST (phospho). Membranes were incubated in the presence of appropriate primary antibody overnight at 4° C. Secondary anti-species-IgG HRP conjugated antibodies were diluted 1:5000 in 5% milk/TBST and incubated in the presence of membranes for 1 hour at room temperature. Membranes were exposed to Thermo Scientific (Waltham, Mass.) Super Signal PICO West ECL detection reagent per manufacturer's recommended protocol and exposed to film to document signal.

Flow Cytometry Cell Cycle Analysis

For dose response cell cycle analysis experiments, cells were treated with a 5-point, 3-fold serial dilution of Compound M plus DMSO control for 24 hours.

Bromodeoxyuridine (BrdU) labeling reagent was added to cells for the final two hours of compound treatment. Cells were then washed with PBS and treated with trypsin to release from the bottom of the plate. Cells were washed and fixed in 90% methanol at −20° C. overnight. Cells were then washed and treated with 2N HCl and 0.5% triton X-100 to denature the DNA, followed by a wash and staining with anti-BrdU Alexa-647 and anti-Cleaved-Caspase-3 FITC antibodies. Finally cells were subjected to RNase treatment and propidium iodide staining. Cells were then analyzed on an LSRII flow cytometer.

Antibodies for Immunoblotting and Flow Cytometry

Immunoblotting

Antibodies detecting total and phospho-MET (Y1234/1235), phospho-Gab1 (Y627), total and phospho-AKT (S473), total and phospho-ERK (T202/Y204), cleaved caspase-3, and cleaved PARP were purchased from Cell Signaling Technologies (Beverly, Mass.). The total β-actin antibody was purchased from Thermo Scientific (Waltham, Mass.). Both secondary anti-rabbit and anti-mouse IgG-HRP conjugated antibodies were purchased from Thermo Scientific (Waltham, Mass.).

Flow Cytometry

The anti-BrdU Alexa-647 antibody was purchased from Invitrogen (Carlsbad, Calif.). The anti-cleaved-caspase-3 FITC antibody was purchased from BD Pharmingen (San Jose, Calif.).

Pharmacodynamic Phospho-Gab1 Assay

Nude mice bearing established TPR-MET xenografts were treated with Compound M at doses of 0.1, 0.5, 0.75, 1, 2, 3, or 10 mg/kg. Three hours post dose, tumors were excised and flash frozen in liquid nitrogen. Tumors were then homogenized in lysis buffer containing protease and phosphatase inhibitors. Lysates were then processed per the SDS-PAGE and Immunoblotting protocol.

Xenograft Models

Animals. Female athymic nude mice 6 weeks of age were obtained from Harlan Laboratories (Indianapolis, Ind.). Animals were housed in sterilized caging and received Harlan Teklad autoclavable or irradiated rodent diet and water ad libitum. All of the procedures were conducted as described in an animal care and use protocol approved by Amgen's Institutional Animal Care and Use Committee. The program of animal care is fully accredited by the Association for Assessment and Accreditation of Laboratory Animal Care International.

Xenograft Studies. MKN45 (3×106 with Matrigel at a ratio of 2:1), SNU-5 (5×106 with Matrigel at a ratio of 2:1) cells were injected subcutaneously in the right flank of female athymic nude mice (n=10 per group). Compound M treatment began when tumors were established (~250 mm3 MKN45; and ~220 mm3 for SNU-5). Compound M was formulated in 30% HPbCD, 10% Pluronic F68. MKN45 tumor bearing mice were administered Compound M at a dose of 3, 10 and 30 mg/kg. SNU-5 tumor bearing mice were administered Compound M at a dose of 0.3, 1, 3, and 10 mg/kg. All mice were dosed by oral gavage once daily. Tumor volume was measured twice weekly with a Pro-Max Fowler Digital Ultra Caliper (Fred Fowler Co., Inc.) as length (mm)×width (mm)×height (mm) and expressed as cubic millimeters. Data are expressed as mean±standard error for each group and plotted as a function of time. The statistical significance of observed differences between growth curves was evaluated by repeated measures ANOVA followed by Dunnett's post hoc test.

Procured Samples and Testing

Formalin fixed paraffin embedded (FFPE) tumor tissue was procured through commercial biospecimen providers. Collection included gastric, gastroesophageal, and esophageal stage IV tumors (n=305). The expression study was performed on 305 non-selected stage IV gastric cancer specimens. MET gene amplification was determined in formalin-fixed, paraffin-embedded (FFPE) gastric, gastroesophageal junction and esophageal adenocarcinoma tissue specimens. Samples were processed according to the manufacturers' instructions. Formalin fixed, paraffin embedded (FFPE) sections are pretreated with a paraffin pretreatment reagent to deparafffinize the sections. Sections with sufficient tumor material are hybridized with MET and chromosome 7 probes and analyzed using a fluorescent microscope. The specimens were stained and scored by the test lab CRO Clarient (A GE Healthcare Company). Samples were classified into three FISH categories based on the evaluation of the number of copies of the MET gene per cell as previously described (Capuzzo 2005). Briefly samples were scored and classified as MET amplified using the following criteria:

Definition 1: MET amplified=FISH Ratio≥2.0; MET non-amplified=FISH Ratio<2

Definition 2: MET amplified=Average MET copies≥5; MET non-amplified=Average MET copies<5

Definition 3: MET amplified=% at least 15 MET copies≥10%; MET non-amplified=% at least 15 MET copies<10%.

Clinical Trial

Compound M is being studied in a phase 1, open-label, dose-escalation trial (Study 20101132) to assess its safety, tolerability, and PK in adult subjects with advanced solid tumors. Eligible subjects have disease that is refractory or resistant to standard treatments or disease for which no standard therapy exists.

Compound M is administered PO on a QD and BID basis and the starting dose was 25 mg. Safety is assessed according to Common Terminology Criteria for Adverse Events (CTCAE) v4.0 criteria and the DLT (dose limiting toxicity) window is 28 days. Dose escalation is proceeding with a modified 3+3+3 design, which defines the MTD (maximum tolerated dose) to have been exceeded when ≥3 subjects in a cohort experience a DLT.

Enrollment is proceeding as follows: if no DLT is observed within the first 28 days in the initial 3 to 4 subjects of a cohort, dose escalation to the next higher dose level cohort will occur. If 1 DLT is observed, 3 additional subjects will be enrolled at the same dose level for a total of at least 6 subjects. If no further DLT(s) are observed, escalation to the next higher dose level cohort will occur. If a second DLT is observed, 3 additional subjects will be enrolled at the same dose level for a total of at least 9 subjects. If no further DLTs are observed, dose escalation to the next higher dose level will occur. If ≥3 DLTs are observed in the first 3 to 9 subjects, then enrolment stops at the third DLT observation and enrolment into a cohort at a lower dose level will be considered.

Dose escalation consists of up to 8 cohorts of 3 to 9 evaluable subjects each. Initially, up to 4 subjects may enroll into a cohort. The planned cohort dose levels are as follows: QD cohorts, cohort 1, 25 mg; cohort 2, 50 mg; cohort 3, 100 mg; cohort 3A, 150 mg; cohort 4, 200 mg; cohort 5, 300 mg; cohort 6, 400 mg; and cohort 7, 500 mg; BID cohorts, cohort B1 100 mg, cohort B2 150 mg, cohort B3 200 mg. The MTD is defined as the highest dose level with an observed incidence of DLT in <33% of subjects enrolled in a cohort. At least 6 subjects will be treated at the MTD. An expansion cohort of up to 20 subjects at the MTD (determined in the dose escalation portion) will be considered to obtain further safety, PK, and efficacy data. If all evaluated dose levels demonstrate an observed incidence of DLT in <33% of subjects, the MTD of Compound M has not been reached and higher dose levels will be considered.

As of 20 Aug. 2012, a preliminary PK analysis of Study 20101132 has been conducted in 24 subjects who remained on study through day 28 after receiving daily oral doses of up to 200 mg Compound M. Mean estimates of elimination half-life ranged from 4.6 to 6.9 hours. Pharmacokinetic dose proportionality was not assessed formally in the small number of subjects; however, exposure to Compound M generally increased with increased dose of Compound M. After 1 week of daily Compound M dosing, mean trough concentrations within cohorts were similar and mean $AUC_{0\text{-}24\,hr}$ accumulation ratios ranged from 0.799 to 1.20 after 28 days of daily oral dosing.

In the 28-day rat toxicology study, exposures observed at the NOAEL ($C_{max}$=12.3 µg/mL, $AUC_{0\text{-}t}$=82.4 µg*hr/mL) exceeded the human mean $C_{max}$ and $AUC_{0\text{-}24\,hr}$ exposures observed in cohort 4 (200 mg) on day 28. For projected efficacy, the human mean trough concentration observed in cohort 3 (100 mg) after 28 days of Compound M dosing (0.131 µg/mL) was similar to the average exposure shown to inhibit c-Met activity by 90% in the TPR-Met xenograft model (0.154 µg/mL).

Safety and Efficacy in Humans

Three clinical studies were ongoing in 2014:

Study 20101132: a phase 1 study in adults with advanced solid tumors;

Study 20120370: a phase 1b/2 study in Asian adults with advanced solid tumors;

Study 20130111: a phase 2 study in adults with advanced solid tumors

Preliminary data are available from 93 subjects enrolled in Study 20101132, of whom 90 (96.8%) have received at least 1 dose of Compound M and 32 (34.4%) have completed the study. No data is available for Study 20120370 or Study 20130111 as of the data cutoff date. Preliminary PK analyses were conducted in 59 subjects in Study 20101132 who received Compound M as either an oral tablet or capsule formulation and remained on treatment through day 28. For 43 subjects who received once daily doses of 25 to 400 mg Compound M as a tablet formulation mean estimates of $T_{1/2,z}$ ranged from 4.6 to 7.4 hours. Compound M exposure generally increased with increased Compound M dose and did not accumulate over time, as AUC0-24 hr accumulation ratios after 28 days of QD dosing ranged between 0.94 and 1.38.

Of the 90 subjects who received Compound M, 89 (98.9%) reported at least 1 treatment-emergent adverse event. Adverse events occurring in at least 10% of subjects were headache (58 subjects [64.4%]), nausea (39 subjects [43.3%]), fatigue (36 subjects [40%]), vomiting (24 subjects [26.7%]), constipation (21 subjects [23.3%]), anemia (19 subjects [21.1%]), hypoalbuminemia (18 subjects [20%]), peripheral edema (17 subjects [18.9%]), decreased appetite (15 subjects [16.7%]), diarrhea, dyspnea, and back pain (14 subjects for each [15.6%]), myalgia and dry skin (11 subjects for each [12.2%]), rash (10 subjects [11.1%]), dizziness and aspartate aminotransferase (AST) increased (9 subjects for each [10%]). The dose of Compound M ranged from 25 mg to 400 mg QD, and from 100 to 250 mg twice daily (BID). The 300-mg dose was identified as an MTD for QD dosing schedule and the recommended phase 2 dose. Twice daily dose escalation is currently ongoing and the MTD has not yet been determined as of the data cutoff date. As of the data cutoff date of 23 Jul. 2014, tumor-response data were available from 84 subjects in Study 20101132, including data on 62 subjects with >1 post-screening Response Evaluation Criteria in Solid Tumors (RECIST) tumor measurement by central read (22 subjects had screening data only). Of these, 1 subject had a complete response and 6 subjects had a partial response. Of these 7 responders, 6 had gastric, gastroesophageal junction (GEJ) or esophageal adenocarcinoma with evidence of MET amplification identified by fluorescence in-situ hybridization assay performed by an experienced local laboratory per regulatory guideline.

Cell Line and Cell Proliferation Assay

All human HCC cell lines were purchased from the American Type Culture Collection (ATCC), Japanese Collection of Research Bioresources (JCRB), Korean Cell line Bank (KCLB), Shanghai Institutes of Biological Sciences (SIBS), Zhongshan Hospital Fudan University (ZHFU), and routinely cultured in 96-well plates in ATCC's recommended growth media in the temperature of 37° C., 5% CO2 and 95% humidity. The next day, cells were treated with different concentrations of Compound M. Cell proliferation was measured after 72 h using CellTiter-Glo® Luminescent Cell Viability Assay Kit (Promega, G7573). Luminescence was measured with a PerkinElmer EnVision® plate reader. Data will not be normalized to a control compound, rather POC (percent of control). POC=(compound treated signal/ DMSO treated signal)*100. POC values were processed with the software of GraphPad Prism version 5 to calculate the absolute $IC_{50}$. Time 0 (T0) reported as broken line on dose response curves were shown in the curve fitting as the percent of the net T3 DMSO control.

Protein Expression Assay

Six HCC cell lines were selected in the treatment of different concentrations of Compound M or DMSO control for 2 h at 37° C. Cells were washed with PBS and lysed using cell lysis buffer (Sigma, C2978). Cell lysates were collected and then centrifuged at 13000 rµm for 20 min at 4° C. to remove cell debris. The supernatant proteins were quantified using BCA protein assay and then mixed with 4×LDS sample buffer plus reducing agent and boiled at 70° C. for 10 mins. The mixtures were centrifuge briefly for immunoblotting and loaded in 4-15% SDS-PAGE gel. Proteins were transferred onto PVDF membrane using Bio-Rad Trans-Blot® Cell System. The membrane was blocked in 5% milk plus 0.1% Tween in TBS at room temperature for 1 h. Membranes were incubated with primary antibodies diluted in blocking buffer at 4° C. overnight. After washes, the membranes were incubated with RDye 800/680 anti-rabbit/mouse antibody (LI-COR Biosciences) diluted in blocking buffer (1:15000) for 1 h at room temperature. The bands were detected with Odyssey System (LI-COR Biosciences). All antibodies were purchased from Cell signaling Technology including anti-p-MET Y1234/1235 (3077S), anti-MET (3148S), anti-p-Gab1 Y627 (3231S), anti-Gab1 (3232S), anti-p-ERK Thr202/Tyr204 (4370S), anti-ERK (9107S), anti-p-AKT Ser473 (4060S), anti-AKT (2920S).

C-MET Fluorescence In-Situ Hybridization (FISH)

MET gene amplification was analyzed by fluorescence in situ hybridization (FISH) by Dako Histology Accessory FISH Kit (K5799) using IQISH Probe Mix MET/CEN-7 (Y5217). The CEP7 centromere probe was used as a reference control according to manufacturer's instructions. Formalin-fixed, paraffin-embedded specimens (cell pellets or PDX models) were prepared for sections followed by deparaffinization and rehydration. H&E staining was performed first. The heat pretreatment was performed in pre-treatment solution at microwave oven for 3 min 50 sec and cool down at RT for 15 min followed by washing. RTU pepsin digested the sections for 6 min at 37° C. (the time can be adjusted according to different sections). After washing, dehydration was conducted completely. The sections with probe proceeded the denaturation at 66° C. for 10 min followed by hybridization at 45° C. for 1-2 h. After stringent washing, section were dehydrated and mounted in the medium containing DAPI, and stored in dark at 4° C. for 15 min before reading. The fluorescence microscope with appropriate filters was used for scanning and identification of relevant tumor area. The signal enumeration for red MET gene and green CEP7 gene were counted in 20 tumor nuclei in a minimum of two areas for determination of MET/CEP7 ratio. The definition of FISH scoring was as follows: ratio <2: MET amplification was not observed; ratio >2: MET amplification was observed; if the ratio is borderline (1.8-2.2), an additional 20 nuclei were counted and recalculated the ration as well as the percentage of nuclei with <2, =2, =15 MET signals per nuclei for the total 40 nuclei.

Met Immunohistochemistry

Met expression was detected by immunohistochemistry in different cell lines or PDX models. First, the FFPE slides were dewaxed and hydrated followed by washing with water. For Met detection by Dako MET IHC pharmDx assay (Lot 20000614) on an automatic immunostainer (Dako), antigen retrieval of FFPE slides were performed at 97° C. for 20 min in EDTA buffer, pH 8.5-9.5, followed by cooling at 65° C., rinsing for 5 min. 4 µm sections were rinsed and incubated with endogenous peroxidase-blocking reagent for 5 min, and then rinsing in TBST. Slides were then labeled with primary antibody against human-Met (Dako). After washing, the HRP labeled polymer and substrate diaminobenzidine (DAB) were added and counterstained using EnVision Hematoxylin kit (Dako) followed by dehydration and sealing. The Met IHC staining intensity was evaluated by the experienced pathologists. The Met IHC scoring criteria was shown as: 0, any tumor cells with membrane staining at intensity of no staining; 1+, at intensity of weak staining; 2+, at intensity of moderate staining; 3+, at intensity of strong staining. High Met expression was defined as the presence of any tumor cells with membrane staining at IHC 3+ intensity.

In Vivo Xenograft Study

Two HCC patient-derived tumor xenograft (PDX) mouse models were established by directly inoculated subcutaneously with primary human HCC tumor tissues into female BABL/c nude mice. Briefly, each mouse (8-10 weeks old) was purchased from Shanghai Laboratory Animal Center (SLAC). All the animal experiments were performed according to the guidelines approved by the Institutional Animal Care and Use Committee (IACUC). The treatment was started when the average size reached about 180 mm$^3$. Mice were allocated randomly into four experiment groups (12 animals per group) according to their tumor sizes. Mice were dosed with vehicle (30% HpbCD, 10% Pluronic F68), or with Compound M at a dose of 3, 10 or 30 mg/kg once per day by oral gavage for 14 days. The tumor size and body weight were measured twice weekly. The length, width, and height of tumors were measured with a caliper. The tumor volume was calculated as L×W×H and expressed in mm$^3$. The percentage of tumor growth inhibition (% TGI=100%−(VTi−VT0)/(VCi−VC0)*100%) was calculated for evaluating anti-tumor efficacy. VTi, mean tumor size in treatment group on the Day i; VT0, mean tumor volume in treatment group on Day 0; VCi, mean tumor size in vehicle group on Day i; VC0, mean tumor size in vehicle group on Day 0.

Data were expressed as means plus standard errors and plotted as a function of time. Statistical significance of observed differences between growth curves of treatment groups and control group was evaluated by repeated measures analysis of covariance of the log transformed tumor volume data with Dunnett adjusted multiple comparisons. Adjusted P<0.05 was considered statistically significant. The analysis was done using SAS proc mixed with model effects of baseline log tumor volume, day, treatment and day-by-treatment interaction with a Toeplitz covariance structure.

Method for Collecting and Preserving Peripheral Blood Samples for the Purposes of Evaluating Circulating Tumor Cells and Evaluating MET Expression on the CTCs Current CTC isolation methods most often process and analyze fresh or only mildly preserved peripheral blood within 96 hrs post collection. This short window poses financial, operating and geographical challenges for CTC analysis. The method disclosed in the present invention for CTC preservation enables freezing of samples for long term storage, batch shipment and batch analysis. The processing of patient blood for CTC preservation utilizes a buffer system consisting of 3 Buffers: Buffer A, Buffer B, and Buffer C.

Buffer System

Buffer A (5× Lyse/Fix Buffer, Beckton Dickenson) and Buffer B (sterile water), were used in combination to lyse/fix whole blood. In more detail, Buffer A was added to Buffer B to make a 1× Lyse/Fix solution as described in the Product Sheet. Instead of the recommended 20 volumes of 1× Lyse/Fix Buffer to 1 volume of whole blood, 5 volumes of 1× Lyse/Fix Buffer to 1 volume of whole blood were used. In addition, the recommended incubation time was changed from 10 to 20 minutes and the incubation temperature was lowered from 37° C. to room temperature.

Buffer C was composed of 500 mM TRIS, pH 7.4/5% BSA/0.09% Sodium Azide (<0.1%). It was used to neutralize residual formalin after 1× lyse/fix buffer has been removed. In addition, Buffer C was used to resuspend the remaining fixed white blood cell pellet and any residual red blood cells before long or short term storage at −80° C. Thawing cell suspensions in Buffer C prevents cell clumping or cell bursting.

CTC Preservation Method

Per patient sample time-point, 7.5 ml of whole blood was collected into an EDTA vacutainer and stored at room temperature until processing but no later than 2 hrs post collection. At time of processing 7.5 ml of patient whole blood was transferred to a 50 ml conical tube and Buffer A/Buffer B mixture was added, combined with the blood and incubated for 20 minutes at room temperature, inverting the sample every 5 minutes. After a 10 minute centrifugation step, supernatant was poured off and the white blood cell pellet was resuspended in 5 ml of Buffer C. Preserved sample was stored at −80° C. until CTC analysis.

CTC Enrichment and Antibody Staining

At time of analysis samples were thawed and immunomagnetically enriched on the CellSearch System (Janssen Diagnostics). Enriched samples were permeabilized and stained manually with a conjugated antibody cocktail containing Dapi and markers for CD45, cytokeratin and MET for 1 hour at room temperature in the dark. After 2 washes samples were transferred to a 96 well glass plate and imaged on a laser scanning cytometer (ThorLabs). Total CTC number and as well as the MET positive CTC subpopulation were tracked.

Identification of MET+/− CTCs

A MET+ CTC in this assay was defined by expression of a marker of epithelial cells (cytokeratin), expression of MET, the absence of expression of a marker of hematopoietic cells (CD45), and the presence of a nucleus (DAPI). To establish positivity thresholds for each conjugated target antibody, commercial cancer patient samples were stained with each respective isotype and 3 standard deviations were added to the mean fluorescence. Target specific fluorescent signal above that threshold defined its marker to be positive. Following positivity thresholds were calculated:

| Antibody 337 | Conjugate | Fluorescence Threshold for Positivity |
|---|---|---|
| CD45 | PE | ≥1.3E6 |
| Cytokeratin | Alexa Fluor 647 | ≥1.4E6 |
| MET | Alexa Fluor 647 | ≥2.7E6 |

Based on these threshold white blood cells (WBC) and MET+/− CTCs could be identified and are as follows:
A. MET positive CTC
   Cytokeratin-Alexa Fluor 647≥1.4E6 and MET-Alexa Fluor 488≥2.7E6 and CD45-PE<1.3E6
B. MET negative CTC
   Cytokeratin-Alexa Fluor 647≥1.4E6 and MET-Alexa Fluor 488<2.7E6 and CD45-PE<1.3E6
C. Contaminating leukocytes (remaining after CTC enrichment)
   CD45-PE≥6.7E5 and Cytokeratin-Alexa Fluor 647<1.4E6

Cell populations A and B were used for survival analysis as described in Example 12.

Example 2

This example illustrates that Compound M is a very selective MET inhibitor. Human kinome selectivity profile for Compound M is represented in FIG. 1. An active site-directed competition binding assay was used to measure binding of Compound M to the active sites of 400 human kinases. Kinase binding levels were reported as percent of control by comparing the signal obtained in the presence or absence of Compound M. Compound M exhibits selectivity for MET (POC=0%) over 399 other kinases.

Example 3

This example demonstrates that cell lines with high level focal amplification of MET exhibit profound sensitivity to Compound M. Compound M sensitivity profile and MET copy number status for a panel of 20 cancer cell lines exhibiting elevated MET copy number are represented in Table 1. IC$_{50}$ values were obtained from 72 hour viability assays testing a dose titration of Compound M. MET copy number status was determined by array comparative genomic hybridization (aCGH) and reported as log 2 ratio of cell line to pooled control DNA from 40 normal donors. Threshold for high vs low MET copy number was set at aCGH log 2 ratio of 2.5. Focal nature of MET copy number increase was defined qualitatively using tiled aCGH results for chromosome 7.

TABLE 1

| Cell Line | Tumor Type | MET Copy Number High[a]/Low[b] | MET Copy Number Focal | IC$_{50}$ |
|---|---|---|---|---|
| Hs 746T | Gastric | High | Yes | 0.003 |
| MKN-45 | Gastric | High | Yes | 0.009 |
| SNU-5 | Gastric | High | Yes | 0.003 |
| NCI-H1993 | NSCLC | High | Yes | 0.017 |
| SNU-620 | Gastric | High | Yes | 0.014 |
| OE33 | Esophagus | High | Yes | 0.003 |
| EBC-1 | NSCLC | High | Yes | 0.008 |
| NUGC-4 | Gastric | Low | Yes | >3 |
| G-361 | Melanoma | Low | No | >3 |
| C32 | Melanoma | Low | No | >3 |
| AU-565 | Breast | Low | No | >3 |
| NCI-H820 | NSCLC | Low | No | >3 |
| HOP-92 | NSCLC | Low | No | >3 |
| NCI-H1648 | NSCLC | Low | Yes | >3 |
| HCC1395 | breast | Low | No | >3 |
| Malme-3M | Melanoma | Low | No | >3 |
| NCI-H1573 | NSCLC | High | Yes | >3 |
| NCI-H2342 | NSCLC | Low | No | >3 |
| Alexander | Liver | Low | No | >3 |
| CAL-54 | Kidney | Low | No | >3 |

[a]High = MET Log2 ratio of >2.5 as defined by a CGH microarray;
[b]Low = MET log2 ratio of ≤2.5, including polysomy and whole arm amplification of chromosome 7, as defined by aCGH microarray;
[c]IC$_{50}$ value from a representative experiment that included a minimum of four replicates.

Figure 2:
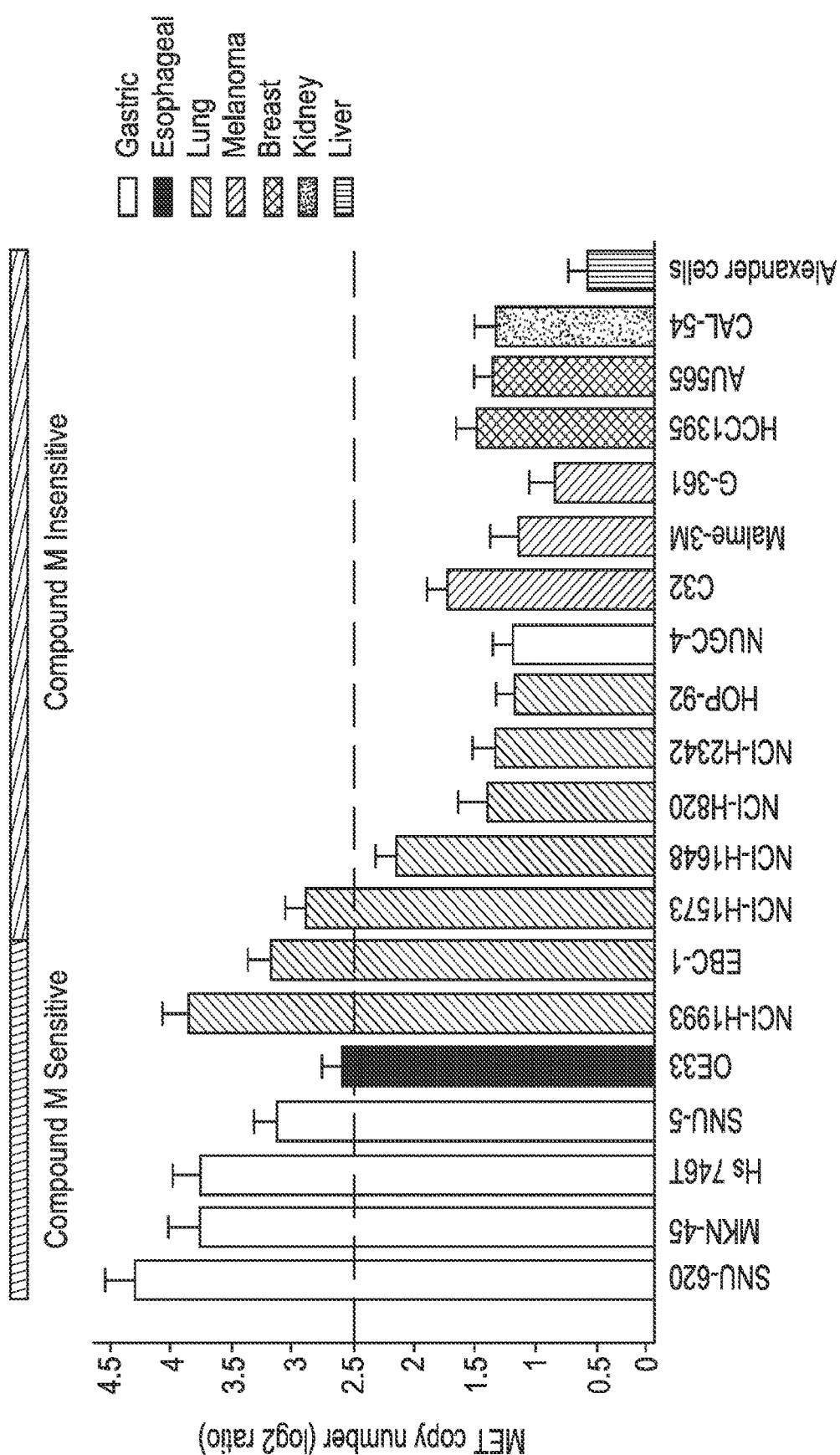
FIG. 2 illustrates MET copy number and Compound M sensitivity status for a panel of 20 cancer cell lines. MET copy number was determined using a human CGH microarray.

Cancer cell lines were profiled in 72 hour viability assays testing a dose titration of Compound M and the results are summarized in FIG. 2, which illustrates that tumor cell lines with elevated MET copy number are sensitive to Compound M. IC$_{50}$ values from the viability assay were used to determine Compound M sensitivity status, binning cell lines with IC$_{50}$ values between 2 and 17 nM as sensitive and cell lines with IC$_{50}$ values >3 μM as insensitive. MET copy number for individual cell lines was determined by array comparative genomic hybridization (aCGH) and reported as log 2 ratio of cell line to pooled control DNA from 40 normal donors. Log 2 ratio of 2.5 (broken red line) was used as a threshold for high vs. low MET copy number.

Example 4

Figure 3:
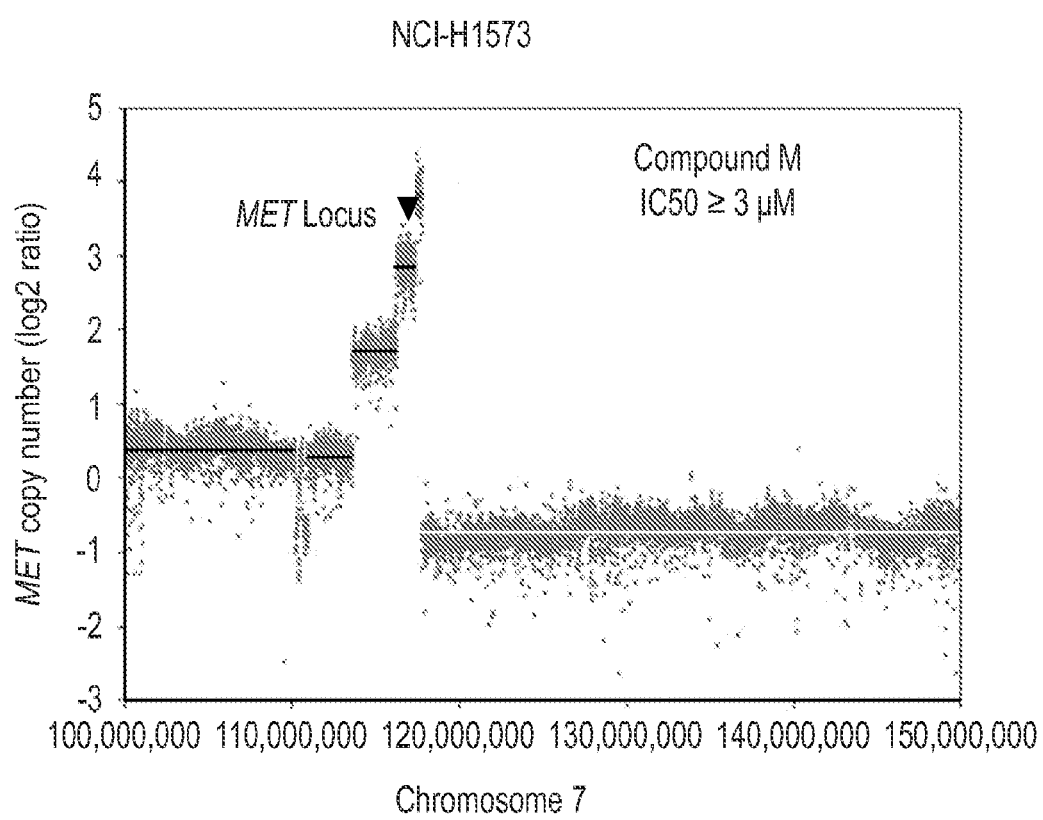
FIG. 3 is a CGH (comparative Genomic Hybridization) profile of MET locus on chromosome 7 in lung cancer cell line NCI-H1573.

This example illustrates that downstream activating mutations in KRAS such as KRAS G12A mutation may confer resistance to Compound M in cell lines with high level focal amplification of MET. aCGH analysis of NCI-H1573 cells identified high level focal amplification of MET (log 2 ratio=2.9) and the results are represented in FIG. 3. Viability profiling of NCI-H1573 cells demonstrated insensitivity to Compound M (viability assay IC$_{50}$>3 μM). Targeted exome sequencing of NCI-H1573 cells using next generation sequencing identified an activating mutation in KRAS (G12A, c.35G>C) that may be responsible for insensitivity to Compound M.

Example 5

Figure 4:
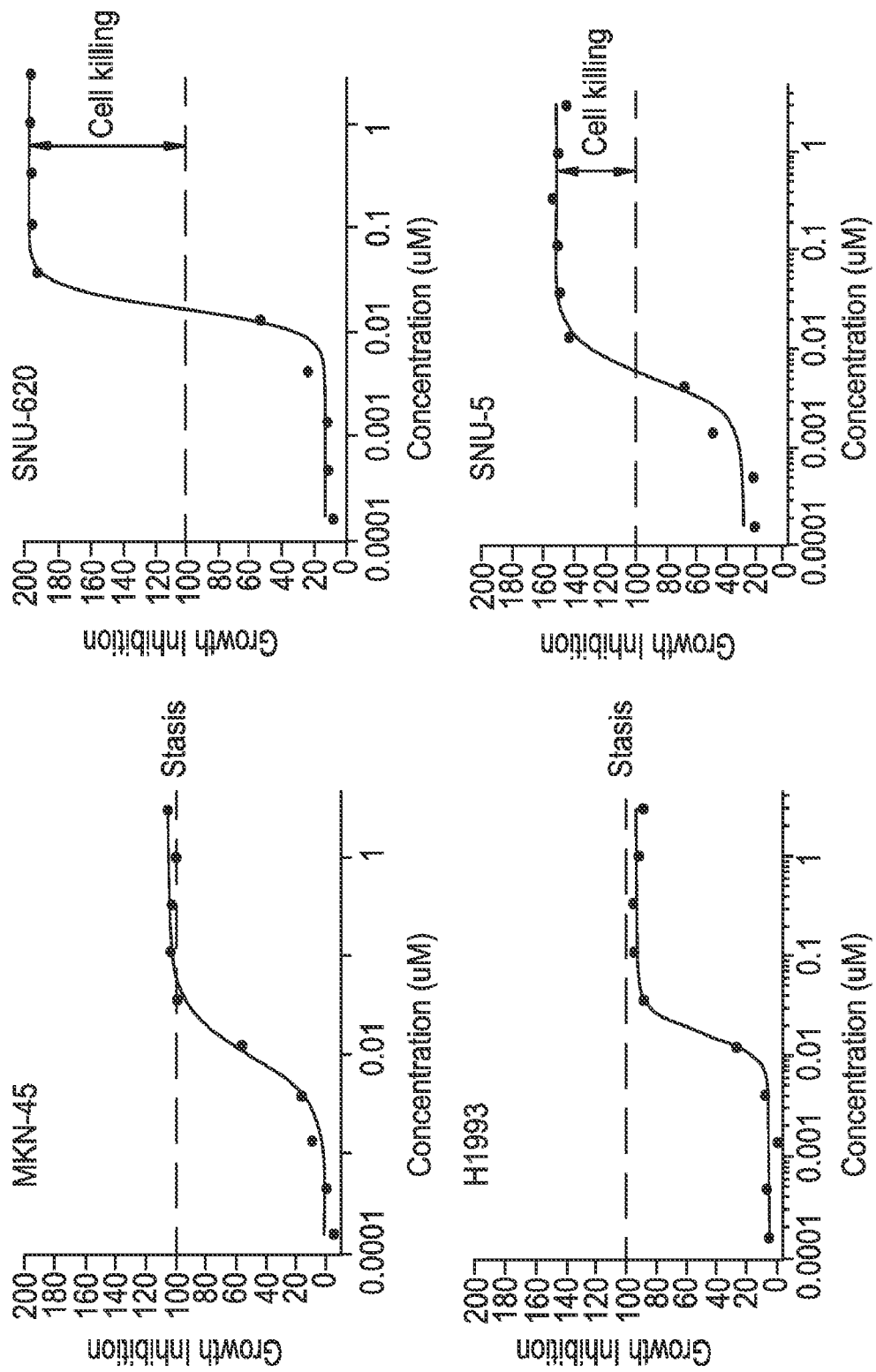
FIG. 4 demonstrates that Compound M inhibits growth in some cell lines and induced cell killing in others. Cell viability results were plotted on a 0-200% growth inhibition scale, with 0%=no effect, 100%=stasis (time 0), and 200%=complete cell death.

This example demonstrates that Compound M exhibits evidence for anti-proliferative and cell killing effects in MET amplified tumor cell lines. FIG. 4 illustrates Compound M viability assay dose response curves for MET amplified cell lines. MET amplified gastric (MKN-45, SNU 620 and SNU 5) and lung (NCI-H1993) cancer cell lines were profiled in 72 hour viability assays testing a dose titration of Compound M. Time 0 and 72 hour DMSO treated controls were used to calculate percent growth inhibition values for each Compound M concentration tested. Percent growth inhibition is reported on a 0-200% scale where 0% is equivalent to no effect (time 72 hour control), 100% is equivalent to stasis (time 0 hour control) and 200% is equivalent to complete cell death. MKN-45 and NCI-H1993 cells exhibit evidence of an anti-proliferative response (maximum effect=100% growth inhibition) to Compound M while SNU-620 and SNU-5 cells exhibit evidence of cell death.

Example 6

Figure 5:
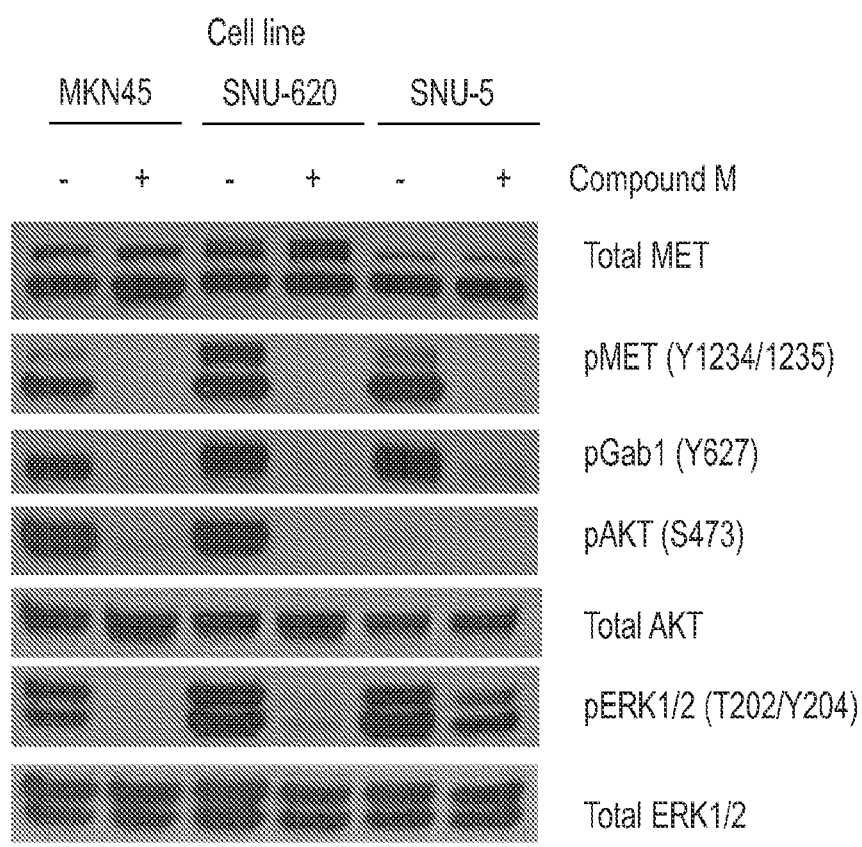
FIG. 5 is Immunoblot analysis of PI3K and MAPK signaling pathways in MET amplified gastric cancer cell lines treated with Compound M. Cells in culture were treated with DMSO or 100 nM of Compound M for 2 h.

In this example it is demonstrated that treatment with Compound M inhibits downstream PI3K and MAPK pathway signaling in MET-amplified gastric cancer cell lines. The results are presented in FIG. 5, which represents immunoblot analysis of PI3K and MAPK signaling pathways in MET amplified gastric cancer cell lines treated with Compound M. MET amplified gastric cancer cell lines (MKN45, SNU-620 and SNU-5) were treated with Compound M (100 nM) or DMSO for 2 hours. Subsequent lysates were analyzed by SDS-PAGE and immunoblot using antibodies detecting total and phospho-MET (Y1234/12335), phospho-Gab1 (Y627), total and phospho-AKT (S473), and total and phospho-ERK 1/2 (T202/Y204). Phosphorylation of MET and Gab1, a key adaptor protein in MET signaling, were inhibited in all three cell lines following treatment with Compound M. Corresponding inhibition of the PI3K and MAPK signaling pathways was also observed as measured by a reduction in phospho-AKT (S473) and phospho-ERK (T202/Y204) respectively.

Example 7

Figure 6A:
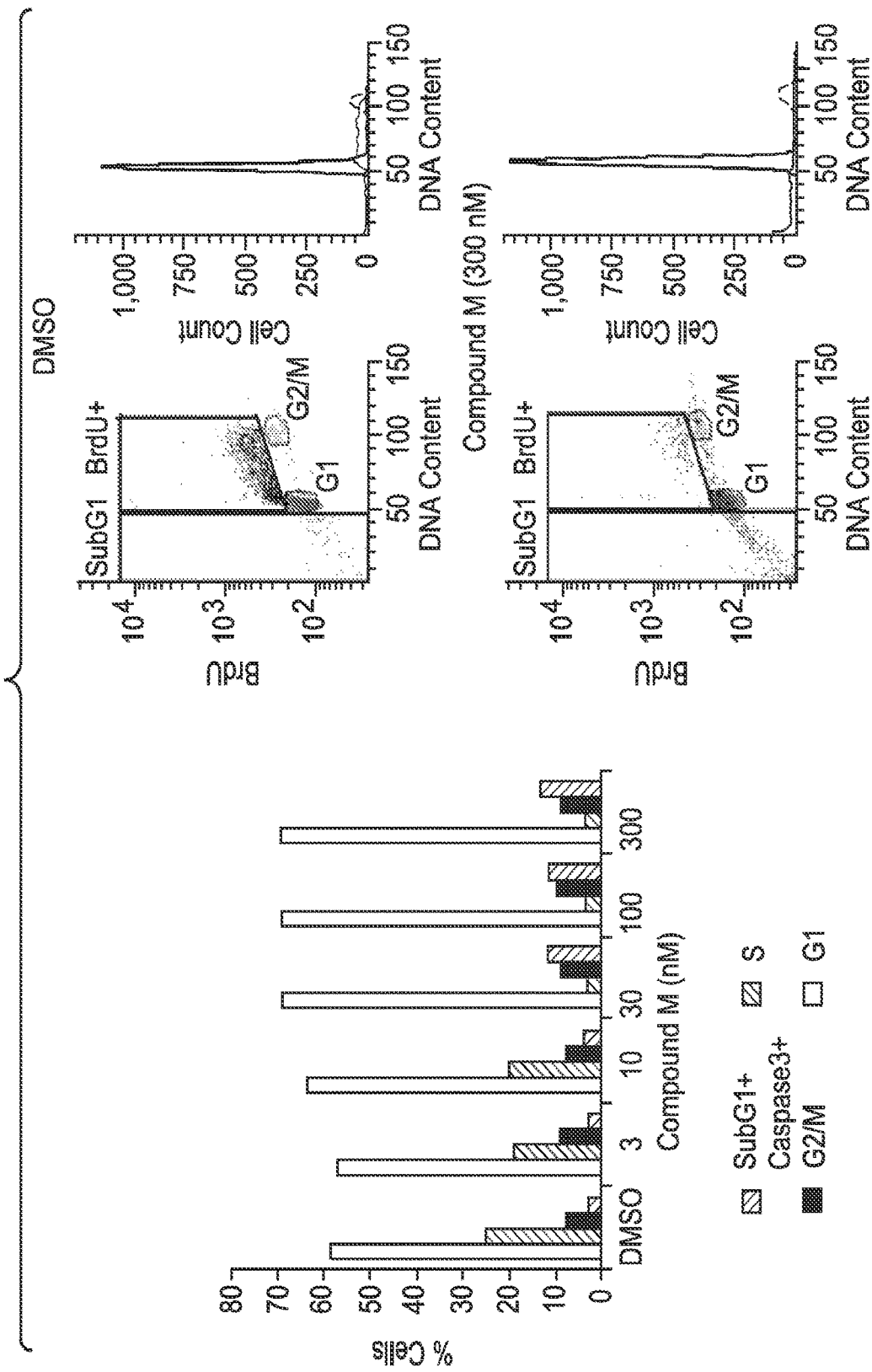
FIG. 6A is a flow cytometry cell cycle analysis of MET amplified gastric cancer cell line MKN-45.
Figure 6B:
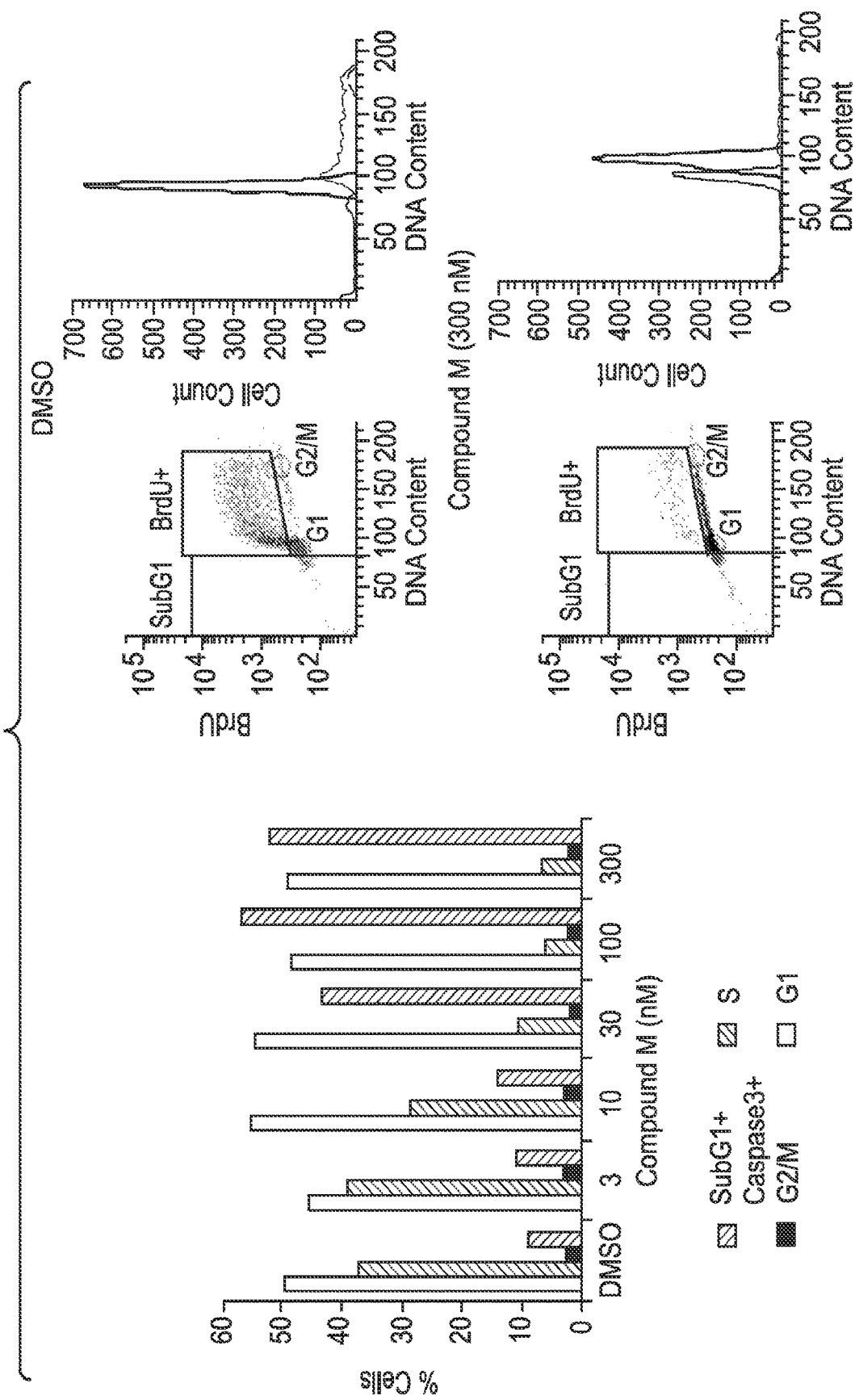
FIG. 6B is flow cytometry cell cycle analysis of MET amplified gastric cancer cell line SNU620. In 6A and 6B cells were treated with DMSO or Compound M for 24 h.
Figure 6C:
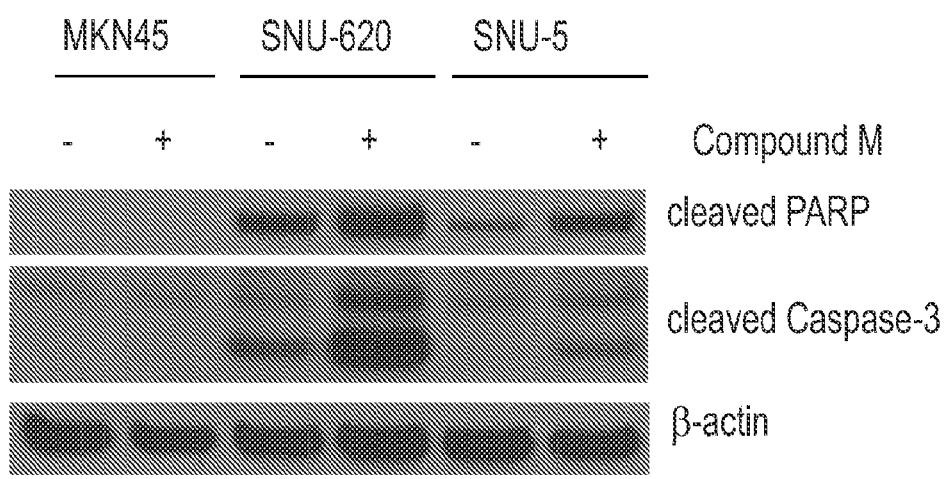
FIG. 6C is Immunoblot analysis of apoptotic markers in MET amplified gastric cancer cell lines treated with Compound M. Cells in culture were treated with DMSO or 30 nM of Compound M for 24 h.

This example demonstrates that Compound M treatment induces anti-proliferative and cell killing effects in MET amplified gastric cancer cell lines. Flow cytometry cell cycle analysis of MET amplified gastric cancer cell line MKN-45 is represented in FIG. 6. MKN-45 cells were treated with a dose titration of Compound M for 24 hours. BrdU labeling was performed during the final 2 hours of compound treatment. Cells were then harvested, fixed, permeabilized and stained with BrdU and caspase-3 antibodies, followed by treatment with RNase and propidium iodide. Cells were then analyzed by flow cytometry to document effects on the cell cycle. Compound M treatment induced an anti-proliferative response in MKN-45 cells with a dose dependent increase in the percentage of cells in the G1 phase of the cell cycle and a corresponding reduction in S-phase positive cells (BrdU+). Flow cytometry cell cycle analysis of MET amplified gastric cancer cell line SNU620 are represented in FIG. 6B. SNU 620 cells were treated as described above. Compound M treatment induced profound cell killing in this cell line as measured by a robust induction in subG1/Caspase-3+ cells. Immunoblot analysis of apoptotic markers in MET amplified gastric cancer cell lines treated with Compound M is represented in FIG. 6C. MKN45, SNU620 and SNU-5 cells were treated with Compound M (30 nM) or DMSO for 24 hours. Subsequent lysates were analyzed by SDS-PAGE and immunoblot using antibodies detecting cleaved PARP, cleaved caspase-3 and β-actin. In agreement with the flow cytometry results in FIG. 6C, SNU-620 cells exhibited evidence of increased cell death following Compound M treatment as measured by elevated cleaved PARP and cleaved caspase-3 levels. No induction of cleaved PARP or cleaved caspase-3 was observed with MKN-45 cells, which was also in agreement with the predominantly anti-proliferative response observed in the flow cytometry analysis. SNU-5 cells demonstrated clear induction of both cleaved PARP and cleaved caspase-3 following treatment with Compound M.

Example 8

Figure 7A:
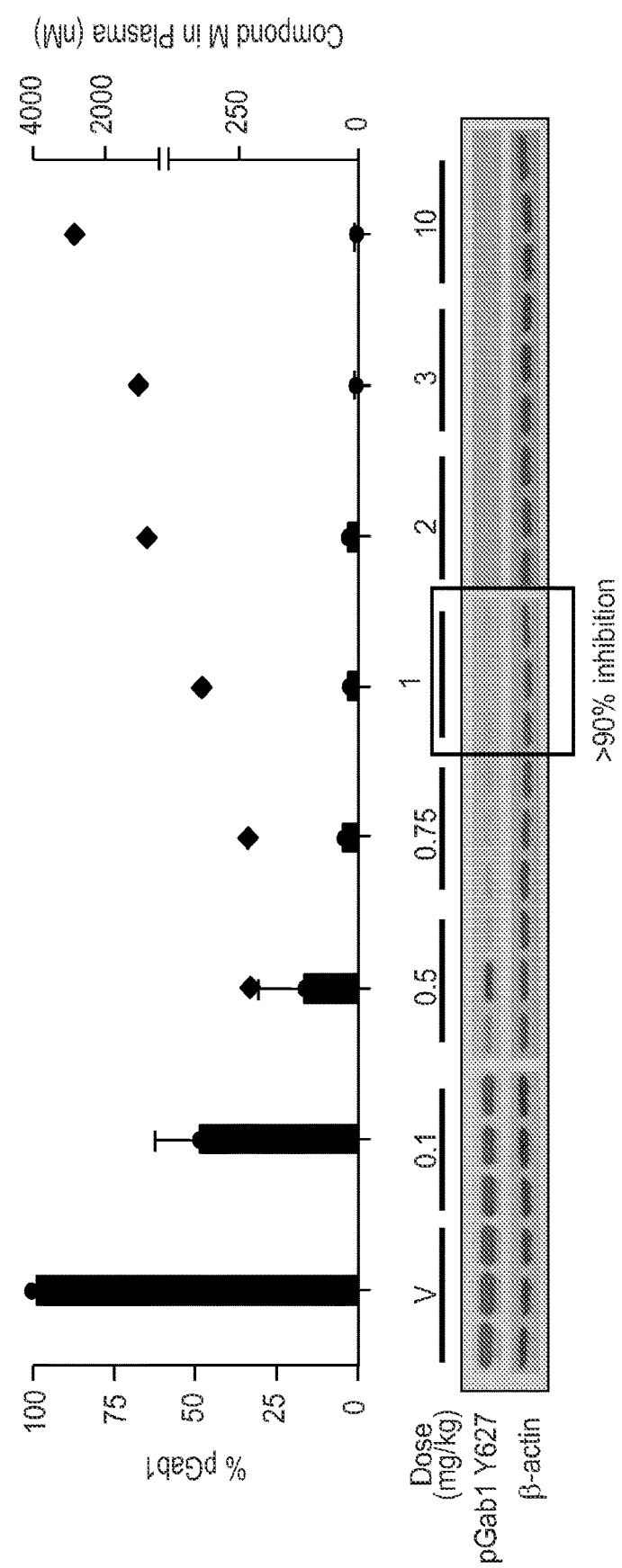
FIG. 7A is Immunoblot analysis of phospho-Gab1 levels in TPR-MET xenografts treated with Compound M.
Figure 8:
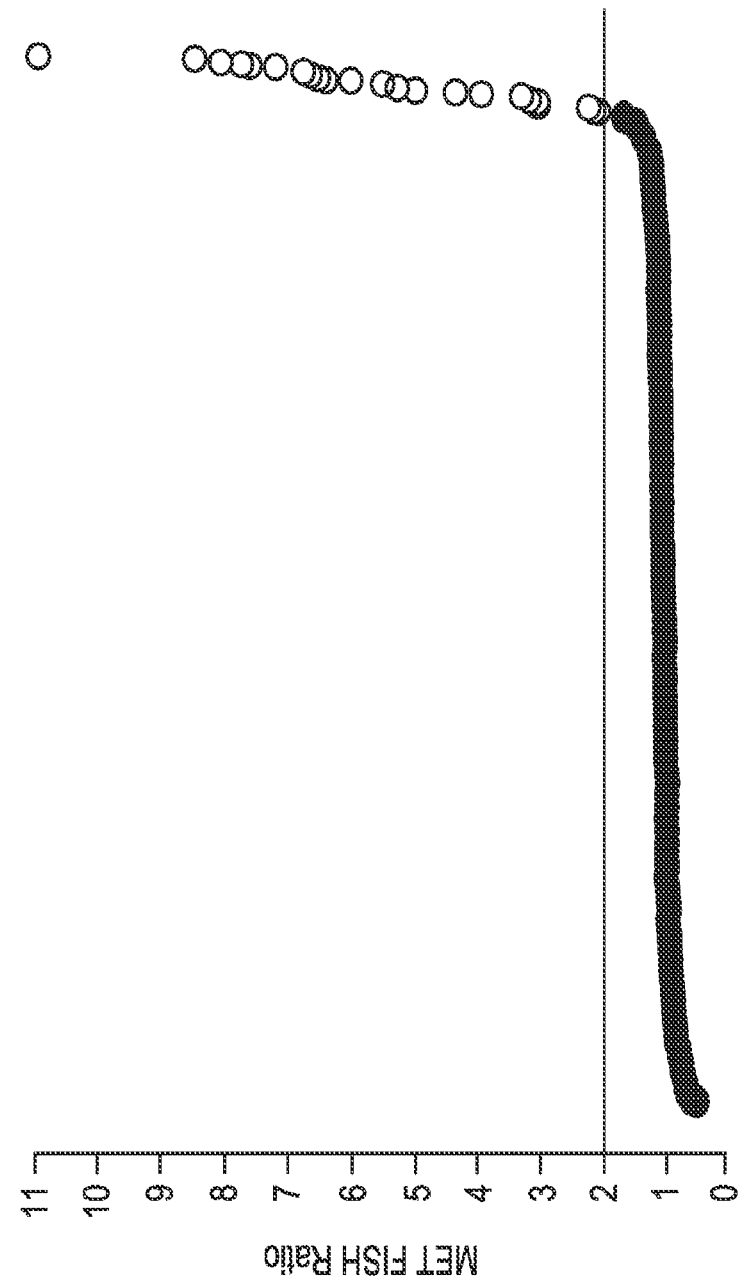
FIG. 8 is a schematic representation of MET amplification frequency in procured and FIH gastric cancer samples. Total number of samples analyzed is 305. Number of samples with MET FISH ratio more than 2 is 12 (4%).

This Example demonstrates that Compound M treatment inhibits MET signaling in tumor xenografts (FIG. 7A) and that Compound M exhibits anti-tumor activity in MET-amplified xenograft models (FIGS. 7B and 7C). Immunoblot analysis of phospho-Gab1 levels in TPR-MET xenografts treated with Compound M is shown in FIG. 7A. Nude mice bearing established TPR-MET xenografts were treated with Compound M at the indicated doses. Tumors were harvested 3 hours post dose and tumor lysates prepared for analysis by SDS-PAGE and immunoblot using antibodies to phospho-Gab1 and β-actin. Phospho-Gab1 levels were quantified using a chemiluminescent imaging system. Compound M treatment inhibited Gab1 phosphorylation in a dose dependent fashion, with greater than 90% inhibition of phoshpo-Gab1 observed at the 1 mg/kg dose.

FIG. 7B shows MET amplified MKN45 gastric cancer tumor xenograft model treated with Compound M. MKN45 cells were injected subcutaneously into the flank of athymic nude mice. When tumors reached 250 mm$^3$, mice were dosed once daily with Compound M at the indicated oral doses. Tumor volumes were measured twice weekly until the conclusion of the study. Compound M achieved robust growth inhibition at all doses tested in the MKN45 xenograft model. FIG. 7C illustrates MET amplified SNU5 gastric cancer tumor xenograft model treated with Compound M. The SNU5 xenograft model was carried out as documented in FIG. 7B. Compound M achieved robust dose dependent anti-tumor efficacy in this model, consistent with the pharmacodynamic modulation of MET signaling.

Example 9

This Example demonstrates correlation of the MET amplification in patients and treatment outcome.

MET amplification in gastric cancer samples was determined as follows, formalin fixed, paraffin embedded (FFPE) sections are pretreated with a paraffin pretreatment reagent to deparafffinize the sections. Sections with sufficient tumor material are hybridized with MET and chromosome 7 probes and analyzed using a fluorescent microscope. Standard FISH scoring practices were used to assess MET amplification. Samples of sufficient quality were reviewed by a pathologist and to assess MET copy number 20 individual, intact nuclei within a sample were identified. Copy number of the MET gene and the chromosome 7 probe were quantitated for each nuclei and an average copy number per nuclei is calculated to yield a score for an individual sample. A ratio of MET to Chromosome 7 (CEN 7) copy number was calculated to yield the ratio score per sample. Initial results were conducted using a laboratory developed test (FISH Ratio 1) and confirmed on a second test at a central lab (FISH Ratio 2) in Table 2.

MET/CEN7 ratios of gastric cancer samples are represented in Table 2.

TABLE 2

| Subject | Diagnosis | Best Response (RESIST) | FISH Ratio 1 (local lab) | FISH Ratio 2 (central lab) |
|---------|-----------|------------------------|--------------------------|----------------------------|
| A | Esophageal | CR | 4.2 | 8.41 |
| B | Gastroesophageal | PD | 2.3 | 3.09 |
| C | Gastric Adenocarcinoma | PR | 4.1 | TBD |
| D | Esophageal | PR | 4.3 | 7.31 |
| E | Gastric Adenocarcinoma | PR | suspected | TBD |
| F | Gastric Carcinoma | PD | 4.24 | 6.54 |
| H | Gastroesophageal Junction | PD | Non-amp | 1.06 |

TABLE 2-continued

| Subject | Diagnosis | Best Response (RESIST) | FISH Ratio 1 (local lab) | FISH Ratio 2 (central lab) |
|---|---|---|---|---|
| I | Esophageal | PD | Non-amp | 1.00 |
| J | Gastric Adenocarcinoma | PD | Non-amp | 1.00 |

CR—complete response, PD—progressive disease, PR—partial response.

These results demonstrate that clinical responses were observed in a subset of patients with MET-amplified tumors. The presence of focal MET amplification as defined by a MET FISH ratio ≥2.0 resulted in a measurable clinical response to Compound M as assessed tumor reduction using RECIST v1.1 criteria. Subjects that did not have focal MET amplification demonstrated no measurable clinical response to Compound M.

Example 10

Figure 9:
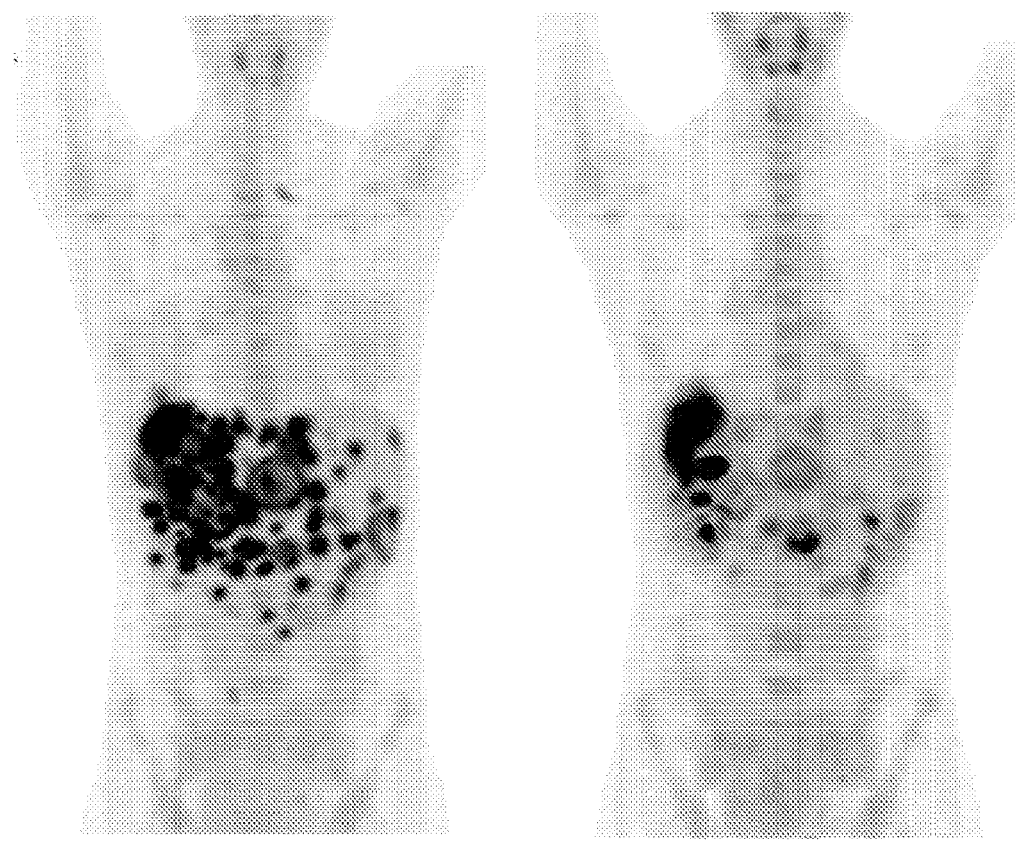
FIG. 9 represents the effect of the treatment with Compound M of a patient with cholangiocarcinoma.

This example demonstrates that Compound M exhibits anti-tumor activity in MET-amplified cholangiocarcinoma tumor (FIG. 9). Met amplification was identified using next generation sequencing assay.

The patient underwent treatment with compound M. The FDG PET/CT scans at baseline (before treatment) and at 5 weeks after daily treatment with compound M, demonstrated significant reduction in metabolic activity of the tumors in the liver, retroperitoneal lymph nodes and supraclavicular lymph nodes.

Example 11

This example demonstrates that Compound M exhibits anti-tumor activity in HCC cell lines with MET amplification and high Met protein expression and in vivo.

The fluorescence in situ hybridization (FISH) analysis and immunohistochemistry (IHC) staining were used to confirm c-MET amplification and high protein expression. The six sensitive and non-sensitive cell lines were selected, including MHCC97H, HCCLM3, JHH-4, JHH-5, SNU-398 and Hep3B. MHCC97H and HCCLM3 cell lines also had high levels of total MET with strong membrane staining (IHC 3+) and MET gene amplification (MET/CEP7>2.0), which were identified as Met-positive HCC. All other cell lines had low MET protein expression (IHC2≤2+) and low MET copy number (MET/CEP7≤2.0), which were c-MET negative. Notably, HCC cell lines with either moderate expression of total c-MET (IHC 2+) or low or no expression of total c-MET (IHC 1+ or 0) did not show dramatic drug sensitivity in the treatment with Compound M. These findings demonstrated a significant and favorable response to Compound M in Met-positive HCC, thus highlighting the relevance between MET gene and protein expression incidence and drug response.

Figure 12:
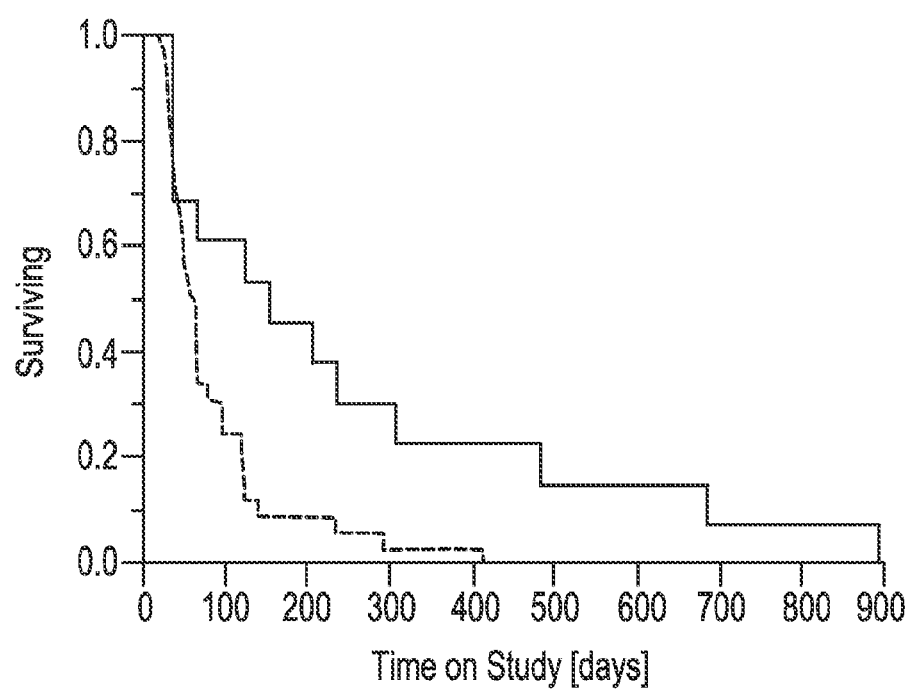
FIG. 12 demonstrates that patients with >10 Met+ CTCs at baseline remained on study longer than patients with at most 10 Met+ CTCs. The difference in median time on study was 91 days.

To determine the effect of Compound M on tumor growth in vivo, an in vivo efficacy study of Compound M in primary hepatocellular carcinoma patient-derived xenograft models (LI0612 and LI1078) was performed. The model LI0612 was chosen because growth of human primary HCC is dependent on MET/HGF signaling pathway. The MET gene copy numbers and protein levels of these two models were characterized using FISH assay and IHC assay, respectively. The model LI0612 was identified MET gene amplification (MET/CEP7>2.0) and high MET protein expression (IHC 3+), whereas the LI1078 model was used as a negative control with non-MET amplification (MET/CEP7<2.0) and MET-low expression (IHC 1+) (FIG. 12).

Figure 10:
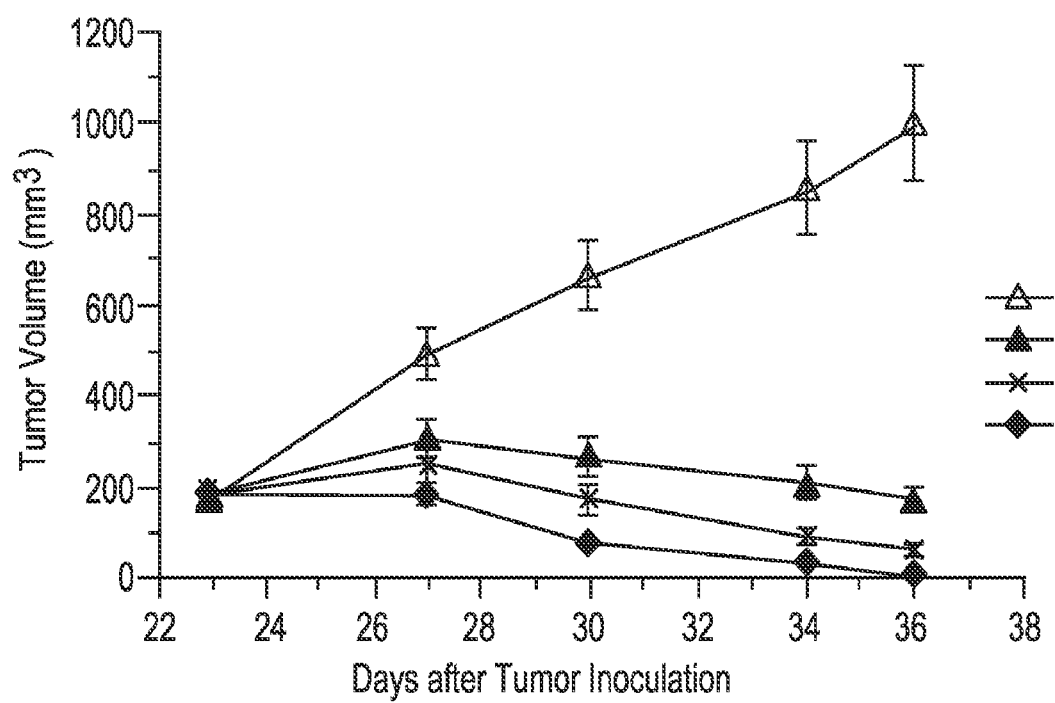
FIG. 10 illustrates anti-tumor efficacy in HCC PDX model LI0612. Treatment with Compound M at doses 3 (dark grey triangle), 10 (cross) or 30 (diamond) mg/kg significantly inhibited tumor growth. Model LI0612 is MET-amplified defined as MET/CEP7 ratio >2.0 (×40) and has high MET expression defined as the presence of any tumor cells with membrane staining at IHC 3+ intensity (×40).
Figure 11:
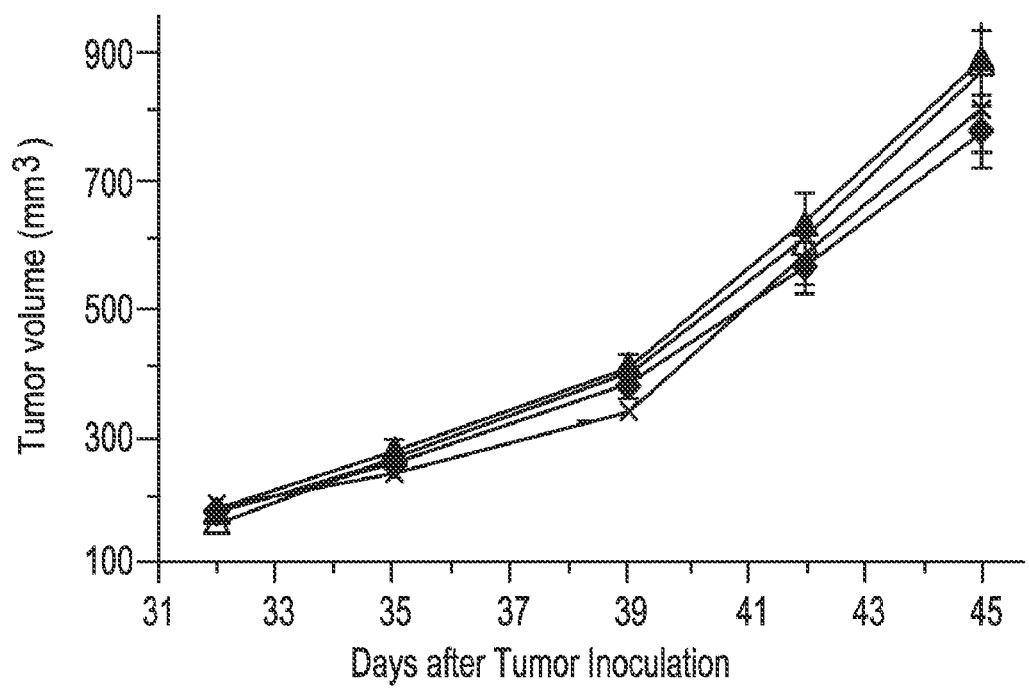
FIG. 11 illustrates no effect of Compound M on tumor growth in HCC PDX LI078 model. Model LI1078 is non-MET-amplified and Met-low expressing HCC with IHC 1+ intensity.

Mice with subcutaneously established tumor tissues were randomly grouped and treated with vehicle or Compound Mat doses of 3, 10 and 30 mg/kg once daily by oral administration for 14 days. For LI0612 model, Compound M significantly inhibited tumor growth compared to the vehicle control group with tumor growth inhibition (% TGI) values of 101.13% (P=0.0003), 114.59% (P<0.0001) and 120.35% (P<0.0001) at doses of 3, 10 and 30 mg/kg, respectively (FIG. 10). Additionally, Compound M exhibited significant tumor regression at 10 and 30 mg/kg, and the effects showed dose dependent responses. For model LI1078, no significant inhibitory effect on tumor growth was observed at all doses of Compound M treatment in the Met negative model with no significant % TGI values of 0.96%, 11.68% and 16.87% at doses of 3, 10 and 30 mg/kg, respectively (FIG. 11). In these models, no significant body weight changed or lost following the administration and Compound M at all dose levels was well tolerated in the anti-tumor study, indicative of acceptable toleration and toxicity. In summary, Compound M demonstrated very high efficacy in the MET-amplified and Met-high expressing PDX model and didn't show encouraging efficacy in the non-MET-amplified and Met-low expressing PDX model.

Example 12

This example demonstrates that greater baseline number of MET positive circulating tumor cells (MET+ CTC) or total CTCs correlate with longer total time on study (TOS) with Compound M.

The results summarized in FIG. 12 demonstrate that patients with >10 MET+ CTCs at baseline remained on study longer than patients with at most 10 MET+ CTCs. The difference in median time on study was 91 days. A Log rank test suggest the effect of MET+ CTC status was significant (p=0.0069).

Figure 13:
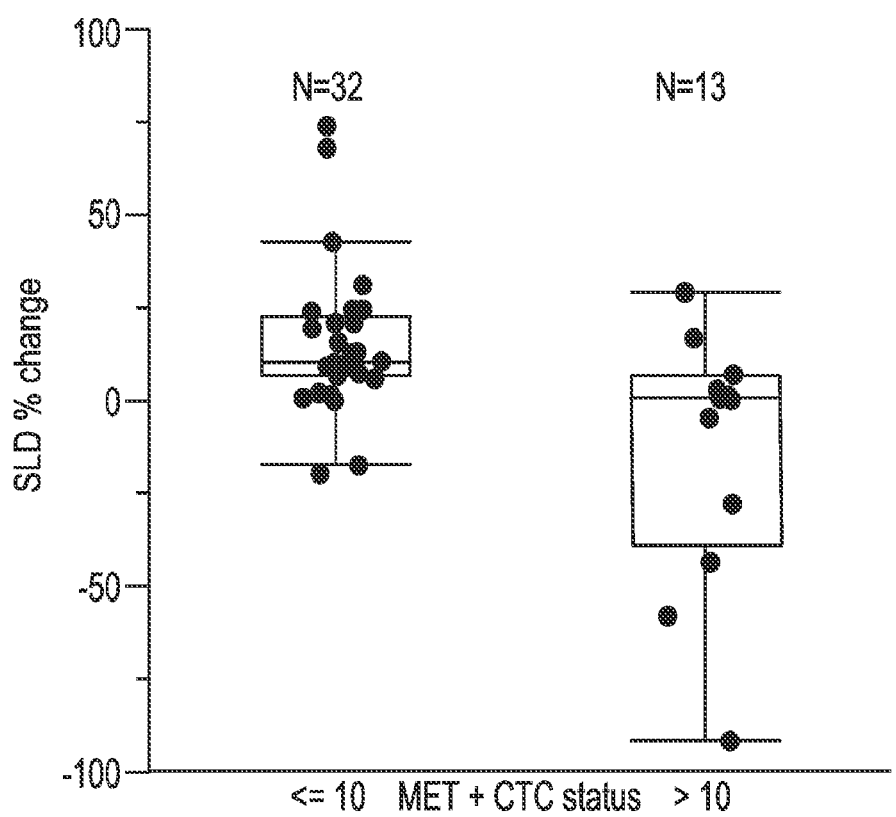
FIG. 13 illustrates that patients with more than 10 Met-positive (Met+) CTCs at baseline had more tumor shrinkage.

FIG. 13 illustrates that patients with >10 MET-positive CTC had more tumor shrinkage. The best percent change in sum of longest diameters (SLD) was tested for an association with baseline MET+ CTC status (above or below 10) after accounting for cohort assignment. Imaging analyses were done to determine disease status for each patient. A skilled practitioner, such as a radiologist, will identify a number of lesions at baseline were identified and were reassessed during the trial to monitor disease status. Each target lesion was characterized by its longest diameter, which is the longest straight line that can be drawn across the lesion. The target lesions were summarized by summing their longest diameters. Changes in this sum of longest diameters (SLD) were used to determine clinical response during the trial. Changes in SLD were commonly reported as percent of baseline SLD. An ANOVA model indicated that there was a difference in SLD change based on MET+ CTC status (p=0.0013). A separate Wilcoxon nonparametric test also suggests a difference in SLD change based on baseline MET+ CTC status (p=0.0035).

Figure 14:
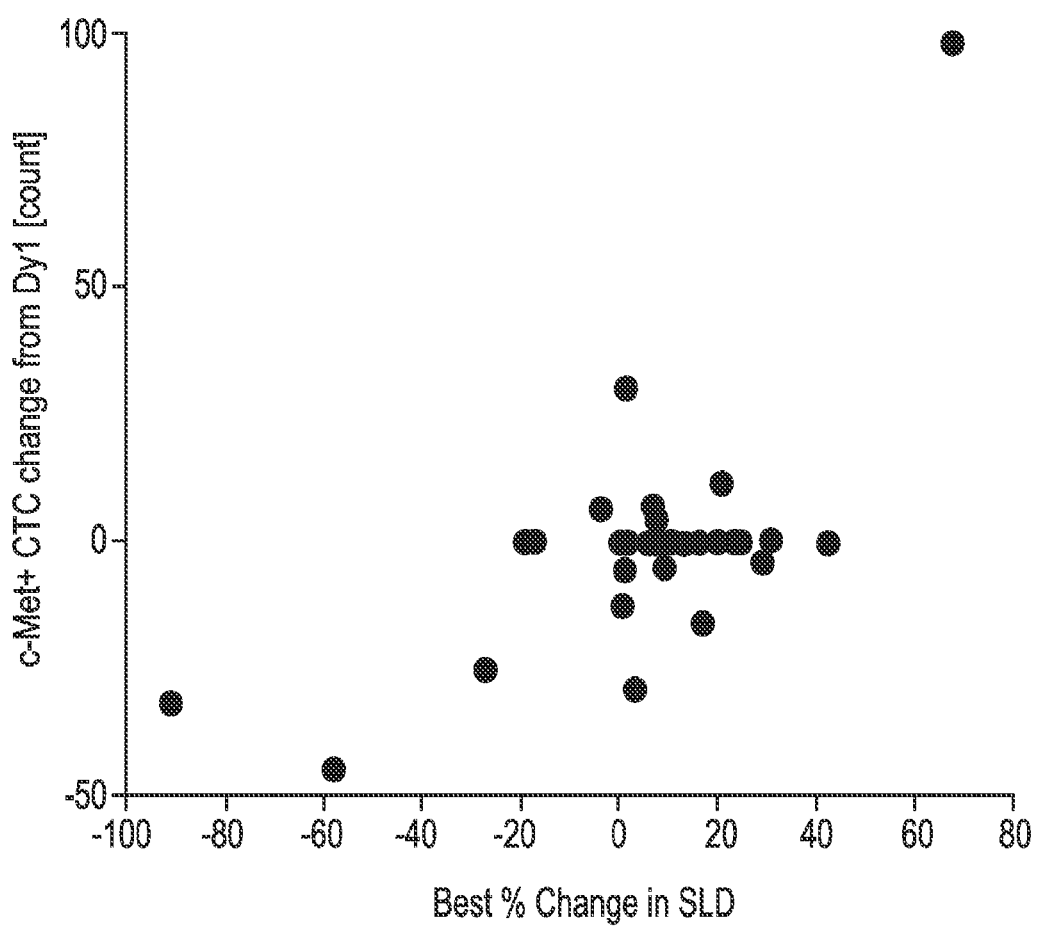
FIG. 14 illustrates that a decrease in Met+ CTC numbers tends to coincide with reduction in tumor burden during treatment with compound M. The best change in SLD (sum of longest diameters) was plotted against the amount of CTC change on the day when the best change in SLD was observed.

FIG. 14 illustrates the association of decrease in MET+ CTC numbers with reduction in tumor burden during treatment with compound M. The best change in SLD was plotted against the amount of CTC change on the day when the best change in SLD was observed.

Taken together, these results demonstrate that (a) baseline numbers of MET+ CTCs associate with treatment response to compound M; (b) expression of MET on CTCs associate with treatment response to Compound M; (c) a decrease in MET+ CTC count during treatment with compound M associates with treatment response to compound M.

Other embodiments will be apparent to those skilled in the art from consideration of the specification and practice of the invention disclosed herein. It is intended that the specification and examples be considered as exemplary only.

What is claimed is:

1. A method of treating a patient diagnosed with gastric cancer, wherein a sample of tumor cells obtained from the patient:
   (i) has the presence of focal amplification of the MET gene; and
   (ii) does not have a mutation at the KRAS gene;
   wherein the presence of focal amplification of the MET gene is defined by FISH as a ratio of MET gene copy number to chromosome 7 copy number; and
   wherein the ratio is 2 or higher,
   the method comprising administering to the patient an amount of
   (6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one) effective to provide a therapeutic benefit.

2. The method according to claim 1, wherein the KRAS gene mutation is G13D, G13C, G12V, G12S, G12R, G12D, G12C, or G12A.

3. The method according to claim 1, wherein focal amplification of the MET gene is determined by detecting increased MET gene copy number.

4. The method according to claim 3, wherein the MET gene copy number is determined by FISH.

5. The method according to claim 1, wherein the ratio is 3 or higher.

6. The method according to claim 1, wherein the ratio is 5 or higher.

7. The method according to claim 3, wherein the MET gene copy number is determined by PCR, qPCR, RT-PCR, comparative genomic hybridization, or next generation sequencing.

8. The method according to claim 1, wherein the presence of focal amplification of the MET gene is defined by Array Comparative Genomic Hybridization as a ratio of MET gene copy number to chromosome 7 copy number.

9. The method according to claim 8, wherein the ratio is 2.5 or higher.

* * * * *